United States Patent
Che et al.

(10) Patent No.: US 7,632,827 B2
(45) Date of Patent: Dec. 15, 2009

(54) ANTI-CANCER PHOSPHINE CONTAINING [AU$^{III}$M(CNC)ML]N+ COMPLEXES AND DERIVATIVES THEREOF AND METHODS FOR TREATING CANCER USING SUCH COMPOSITIONS

(75) Inventors: Chi Ming Che, Hong Kong (HK); Raymond Wai Yin Sun, New Territories (HK); Zhen Fan Yang, Sai Ying Pun (HK); Carrie Ka Lei Li, New Territories (HK)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 11/961,631

(22) Filed: Dec. 20, 2007

(65) Prior Publication Data

US 2008/0166429 A1  Jul. 10, 2008

Related U.S. Application Data

(60) Provisional application No. 60/870,909, filed on Dec. 20, 2006.

(51) Int. Cl.
*A61K 31/555* (2006.01)
*C07F 1/12* (2006.01)

(52) U.S. Cl. .............................. 514/188; 546/2; 546/4; 546/10

(58) Field of Classification Search .................. 514/188; 546/2, 4, 10
See application file for complete search history.

(56) References Cited

OTHER PUBLICATIONS

Li, C. K. et al.: Anticancer cyclometalated [AuIII m($\hat{C}\,\hat{N}\,C$)mL]n+ compounds: Synthesis and cytotoxic properties. Chem. Eur. J., vol. 12, pp. 5253-5266, 2006.*

Becker, "Human thioredoxin reductase is efficiently inhibited by (2,2':6',2"-terpyridine)platinum(II) complexes. Possible implications for a novel antitumor strategy", *J. Med. Chem.*, 44(17):2784-2792 (2001).

Che, "Gold(III) porphyrins as a new class of anticancer drugs: cytotoxicity, DNA binding and induction of apoptosis in human cervix epitheloid cancer cells", *Chem. Commun.*, (14):1718-1719 (2003).

Coronnello, "Mechanisms of cytotoxicity of selected organogold(III) compounds", *J. Med. Chem.*, 48(21): 6761-6765 (2005).

Giovagnini, "Synthesis, characterization, and comparative in vitro cytotoxicity studies of platinum(II), palladium(II), and gold(III) methylsarcosinedithiocarbamate complexes", *J. Med. Chem.*, , 48(5):1588-1595 (2005).

Kumar and Asuncion, "DNA binding studies and site selective fluorescence sensitization of an anthryl probe", *J. Am. Chem. Soc.*, 115:8547-8553 (1993).

Hollis and Lippard, "Aqueous Chemistry of (2,2',2"-Terpyridine)gold(III). Preparation and Structures of [Au(terpy)Cl]Cl$_2$.3H$_2$O and the Mixed-Valence Au(I)-Au(III) Salt [Au(terpy)Cl]$_2$[AuCl$_2$]$_3$[AuCl$_4$]", *J. Am. Chem. Soc.*, 105:4293-4299 (1983).

Long and Barton, "On demonstrating DNA intercalation", *Acc. Chem. Res.*, 23, 271 (1990).

Shaw III, "Gold-based therapeutic agents", *Chem. Rev.*, 99(9):2589-2600 (1999).

Wong, "Application of 2,6-Diphenylpyridine as a Tridentate [$\hat{C}\,\hat{N}\,\hat{C}$] Dianionic Ligand in Organogold(III) Chemistry. Structural and Spectroscopic Properties of Mono- and Binuclear Transmetalated Gold(III) Complexes", *Organometallics*, 17(16):3505-3511 (1998).

Yam, "Luminescent Gold(III) Alkynyl Complexes: Synthesis, Structural Characterization, and Luminescence Properties", *Angew. Chem. Int. Ed. Engl.*, 44:3107-3110 (2005).

Yang, "Novel Au(III) complexes of aminoquinoline derivatives: crystal structure, DNA binding and cytotoxicity against melanoma and lung tumor cells", *Dalton Trans.*, 3419-3424 (2003).

* cited by examiner

*Primary Examiner*—Charanjit S Aulakh
(74) *Attorney, Agent, or Firm*—Pabst Patent Group LLP

(57) ABSTRACT

Gold(III) phosphine complexes $[Au_m(CNC)_mL]^{n+}$ (where HCNCH=2,6-diphenylpyridine) and their use as anti-tumor agents are disclosed. Notable results for the appearance of new potential anti-tumor application of these gold(III) complexes are reported. The described complexes show promising cytotoxic properties toward cancer cells in both in vitro and in vivo studies.

11 Claims, 10 Drawing Sheets time = 0 h time = 72 h 8.0    7.5    7.0    6.5    6.0   $^1$H(ppm)

ANTI-CANCER PHOSPHINE CONTAINING [AU$^{III}$M(CNC)ML]N+ COMPLEXES AND DERIVATIVES THEREOF AND METHODS FOR TREATING CANCER USING SUCH COMPOSITIONS

CROSS-REFERENCE TO RELATED APPLICATIONS

This application claims benefit of and priority to U.S. Provisional Patent Application No. 60/870,909 filed on Dec. 20, 2006, and which is incorporated herein in its entirety.

FIELD OF THE INVENTION

The invention relates to gold(III) phosphine complexes as anti-tumor and antiviral agents, pharmaceutical compositions including these complexes, and methods for treatment of cancer and viral diseases using such compositions.

BACKGROUND OF THE INVENTION

The success of cisplatin and its derivatives as anticancer agents has stimulated the development of metal-based compounds, including that of gold, for anticancer treatment [C. F. Shaw III, Chem. Rev. 1999, 99, 2589]. In this context, extensive investigations on the biological properties of gold(I) and gold(III) have been reported. The development of gold(III) compounds as potential anti-cancer agents has been hampered by their poor stability in solution. Very few cytotoxic gold(III) compounds such as [Au(bipy$^c$-H)(OH)][PF$_6$] (bipy$^c$-H=deprotonated 6-(1,1-dimethylbenzyl)-2,2'-bipyridine), [Au(dmamp)Cl$_2$] [dmamp=2-(dimethylaminomethyl)phenyl], and gold(III) Tetraarylporphyrins [C.-M. Che, R. W.-Y. Sun, W.-Y. Yu, C.-B. Ko, N. Zhu, H. Sun, Chem. Commun. 2003, 1718], have been reported to have significant stability.

The stability of metal compounds is usually enhanced by multi-dentate chelating ligands. Lippard and co-workers first reported the use of the tridentate terpyridine ligand (terpy) to generate a planar gold(III) metallointercalator [L. S. Hollis, S. J. Lippard, J. Am. Chem. Soc. 1983, 105, 4293]. Messori, Orioli and Coronnello also reported a number of gold(III) compounds containing 6-(1,1-dimethylbenzyl)-2,2'-bipyridine ligands [M. Coronnello, B. Mini, B. Caciagli, M. A. Cinellu, A. Bindoli, C. Gabbiani, L. Messori, J. Med. Chem. 2005, 48, 6761; L. Giovagnini, L. Ronconi, D. Aldinucci, D. Lorenzon, S. Sitran, D. Fregona, J. Med. Chem. 2005, 48, 1588]. Guo and co-workers recently reported the synthesis of [Au(Quinpy)Cl]Cl [where HQuinpy=N-(8-quinolyl)pyridine-2-carboxamide] and its derivatives. These gold(III) compounds are cytotoxic and bind to DNA [T. Yang, C. Tu, J. Zhang, L. Lin, X. Zhang, Q. Liu, J. Ding, Q. Xu, Z. Guo, Dalton Trans. 2003, 3419]. In addition, Coronnello, Messori and Fregona and their co-workers have recently shown that gold(III) induced cytotoxicity may proceed via an induction of apoptosis.

The synthesis and study of a series of gold(III) porphyrins that exhibit potent in vitro and in vivo anti-cancer properties toward hepatocellular carcinoma and nasopharyngeal carcinoma has been reported. As demonstrated by DNA microarray and proteomic analyses, the gold(III) tetraarylporphyrins up-regulated the transcription and translation of a number of apoptosis-related gene and protein expressions. [Au$_m$(CNC)$_m$ L]$^{n+}$ compounds (where HCNCH=2,6-diphenylpyridine, and L=phosphine-containing ligand, Scheme 1), were first developed and reported in 1998 [K.-H. Wong, K.-K. Cheung, M. C.-W. Chan, C.-M. Che, Organometallics 1998, 17, 3505].

It is an object of the present invention to provide gold(III) porphyrins which are more robust in solution and therefore more effective in treatment of tumors.

SUMMARY OF THE INVENTION

Methods of using gold(III) complexes as anti-tumor agents are described. In one embodiment, cancer cell death is achieved by administering to a patient in need thereof a composition comprising an effective amount of a gold(III) complex. The gold (III) complexes can be represented by structural formula I and II:

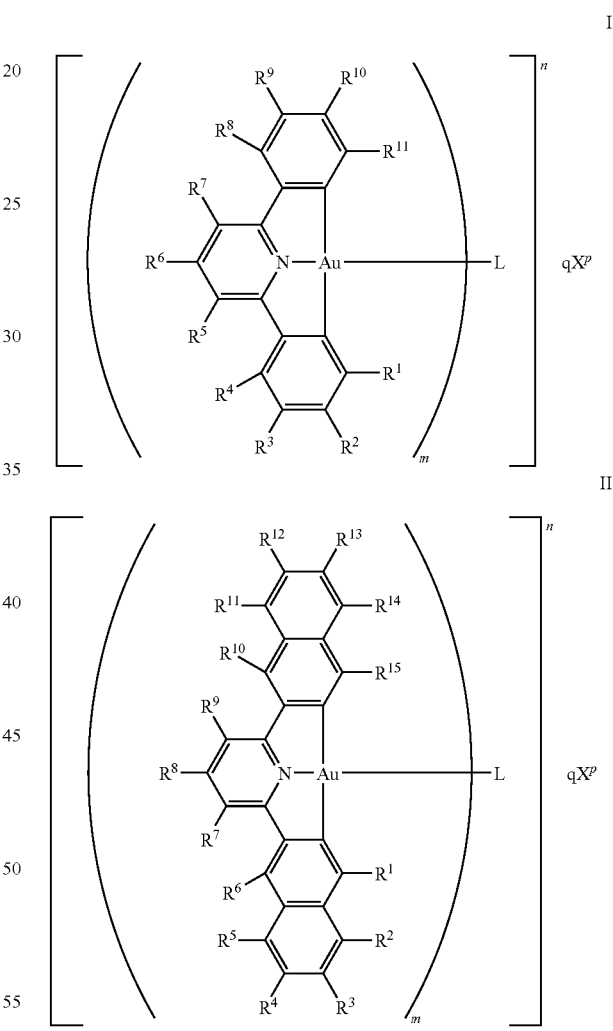

or a pharmaceutically acceptable salt thereof, wherein:

R$^1$-R$^{15}$ are each independently hydrogen, alkyl, substituted alkyl, alkenyl, substituted alkenyl, alkynyl, substituted alkynyl, phenyl, substituted phenyl, halo, nitro, hydroxyl, alkoxyl, substituted alkoxyl, phenoxyl, substituted phenoxyl, aroxyl, substituted aroxyl, alkylthio, substituted alkylthio, phenylthio, substituted phenylthio, cyano, isocyano, substituted isocyano, carbonyl, substituted carbonyl, carboxyl, substituted carboxyl, amino, substituted amino, amido, substituted amido, sulfinyl, substituted sulfinyl, sulfonyl, substituted sulfonyl, sulfonic acid, substituted sulfonic acid, phosphonato, substituted phosphonato, phosphoramide, substituted phosphoramide, $C_1$-$C_{20}$ cyclic, substituted $C_1$-$C_{20}$ cyclic, heterocyclic, substituted heterocyclic, amino acid, peptide, or polypeptide group;

ligand L is independently —P-donor ligand;

each $X^p$ is independently a pharmaceutically acceptable counter-ion;

m is an integer ranging from 1 to 10;
n is an integer ranging from −10 to 100;
p is an integer ranging from −3 to 3;
q is equal to the absolute value of n/p;
$qX^p$ is absent when n is 0; and
a pharmaceutically acceptable carrier.

Preferred values for m are 1 to 10, and for n are −10 to 100.

DETAILED DESCRIPTION OF THE PREFERRED EMBODIMENTS

Figures 1, 2, 3, 3D:
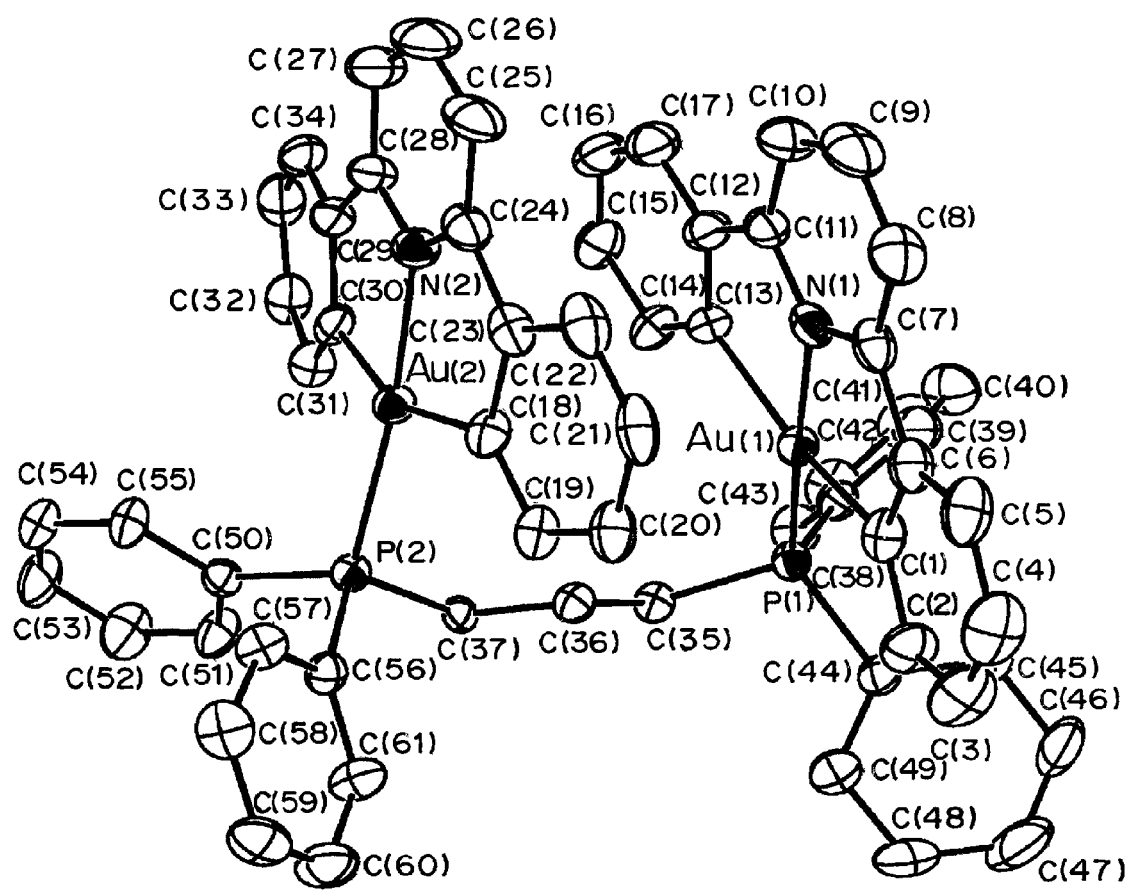
FIG. 1 shows ORTEP drawings with atom-numbering scheme of phosphine-containing $[Au^{III}_m(CNC)_mL]^{n+}$ compounds in accordance with the present invention. Hydrogen atoms and solvent molecules are omitted for clarity. Thermal ellipsoids are drawn at the 30% probability level.
FIG. 2 shows the $^1$H NMR spectra of compound 3d in $D_2O$/[D6] DMSO (9:1) at time=(a) 0 and (b) 72 h.
Figures 1, 2, 3, 3H:
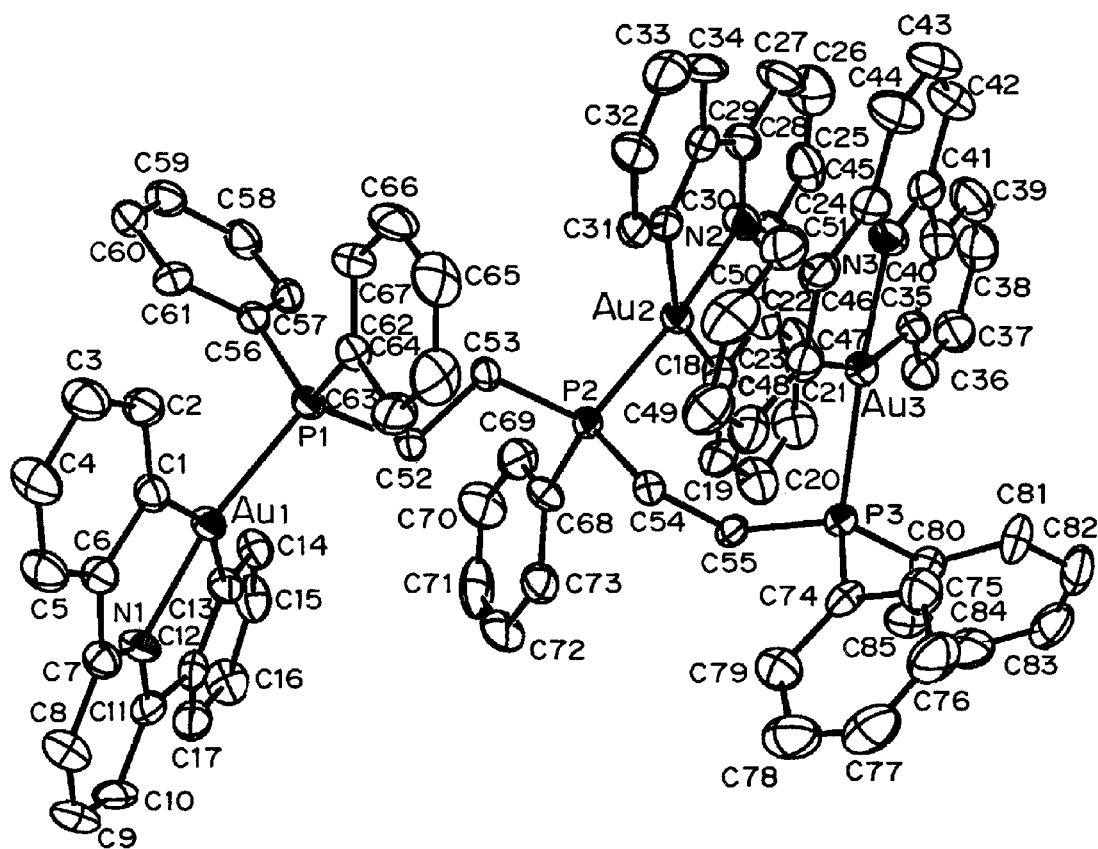

Gold(III) [or Au(III) or $Au^{III}$] phosphine complexes $[Au^{III}_m(CNC)_mL]^{n+}$ are used as anti-tumor and anti-viral agents and as pharmaceutical compositions for combating cancer. The pharmaceutical compositions contain different synthetic $[Au^{III}_m(CNC)_mL]^{n+}$ compounds in amounts effective to induce cancer cell death.

The cationic $[Au_m(CNC)_mL]^{n+}$ (for m=1, n=1, L=phosphine ligand) compounds were predicted to be structurally analogous to the classical metallointercalating [Pt(terpy)L]$^+$ compounds [K. Becker, C. Herold-Mende, J. J. Park, G. Lowe, R. H. Schirmer, *J. Med. Chem.* 2001, 44, 2784]. This class of compounds should be highly robust in solution, since the dianionic nature of CNC ligand would stabilize the electrophilic gold(III), making its reduction to gold(II) and gold(I) at negative reduction potential. One should also be able to make structural modifications to the $[Au_m(CNC)_mL]^{n+}$ compounds through ligand substitution reactions of L (phosphine ligand), which would be highly useful for studying the relationship between structure and cytotoxicity. By using appropriate polydentate phosphine ligands, polynuclear gold(III) compounds comprising more than one [Au(CNC)]$^+$ moiety (m=2 or 3) could be obtained. It is understood that the CNC molecule and the gold(III) center may not form a charge neutral complex. For instance, the net positive charge on the gold(III) may be greater than the absolute net negative charge of the CNC molecule; or the net positive charge on the gold(III) may be less than the absolute net negative charge of the CNC molecule. In view of this, there should be least one anion or counter-ion coordinated to the gold(III) complex for charge neutralization. Accordingly, the phrase "pharmaceutically acceptable salt," as used herein, includes salts formed from charged gold(III) complex and the anion or counter-ion.

I. Definitions

As used herein, the term "CNC" refers to a molecule of either one of the following chemical structures:

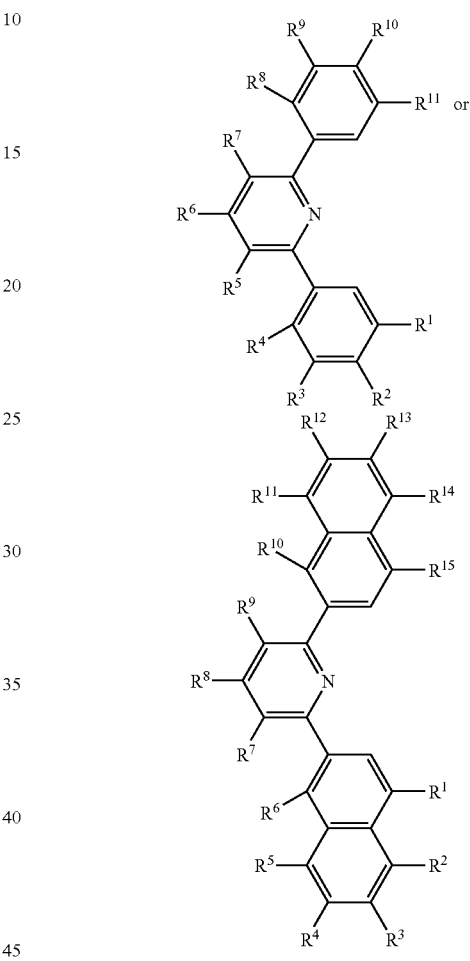

where $R^1$-$R^{15}$ are each independently hydrogen, alkyl, substituted alkyl, alkenyl, substituted alkenyl, alkynyl, substituted alkynyl, phenyl, substituted phenyl, halo, nitro, hydroxyl, alkoxyl, substituted alkoxyl, phenoxyl, substituted phenoxyl, aroxyl, substituted aroxyl, alkylthio, substituted alkylthio, phenylthio, substituted phenylthio, phenylthio, substituted phenylthio, cyano, isocyano, substituted isocyano, carbonyl, substituted carbonyl, carboxyl, substituted carboxyl, amino, substituted amino, amido, substituted amido, sulfinyl, substituted sulfinyl, sulfonyl, substituted sulfonyl, sulfonic acid, substituted sulfonic acid, phosphonato, substituted phosphonato, phosphoramide, substituted phosphoramide, $C_1$-$C_{20}$ cyclic, substituted $C_1$-$C_{20}$ cyclic, heterocyclic, substituted heterocyclic, amino acid, peptide, or polypeptide group As used herein, the phrase "counter-ion" refers to an ion associated with a positively or negatively charged gold(III) complex. Non-limiting examples of counter-ions include fluoride, chloride, bromide, iodide, sulfate, phosphate, trifluoromethanesulfonate, acetate, nitrate, perchlorate, acetylacetonate, hexafluoroacetylacetonate, sodium and potassium.

As used herein, the term "$[Au^{III}_m(CNC)_mL]^{n+}$ complex or complexes" refers to complex of gold(III) metal bound to any CNC molecule and to any phosphine molecule The gold(III) ion can have one or more various neutral, positively or negatively charged CNC molecule(s). The structure of $[Au^{III}_m(CNC)_mL]^{n+}$ complexes can be either in monomeric, dimeric or polymeric form. Also, they can exist as a single molecule or aggregated molecules.

As used herein, the phrase of "pharmaceutically acceptable carrier" means a carrier combination of carrier ingredients approved by a regulatory agency of the Federal or a state government or listed in the U.S. Pharmacopoeia or other generally recognized pharmacopoeia for use in animals, mammals, and more particularly in humans. Non-limiting examples of pharmaceutically acceptable carriers include liquids, such as water and oils, including those of petroleum, animal, vegetable, or synthetic origin. Water is preferred vehicle when the compound of the invention is administered intravenously. Saline solutions and aqueous dextrose and glycerol solutions can also be employed as liquid vehicles, particularly for injectable solutions.

As used herein, the term "patient" refers to any animal, preferably a human.

II. Methods Of Treatment

The compositions are useful for induction of cancer cell death (including but not limited to apoptosis) of cancer cells by administering to a patient afflicted with a responsive form of cancer a composition comprising an effective amount of one or more $[Au^{III}_m(CNC)_mL]^{n+}$ complexes. The $[Au^{III}_m(CNC)_mL]^{n+}$ complexes can be represented by structural formulas I or II, or a pharmaceutically acceptable salt thereof:

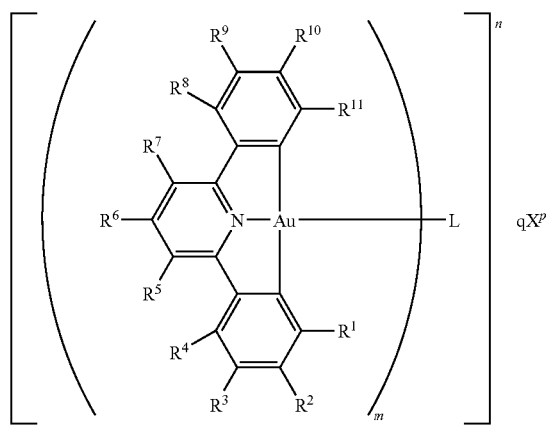

I

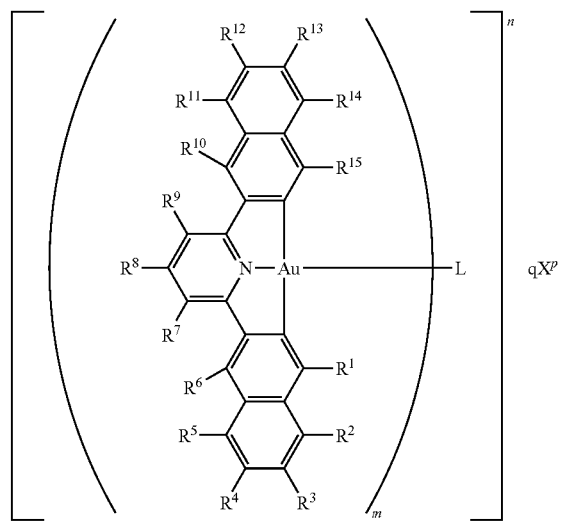

II

As used herein, the term "L" in structural formulae I or II refers to an ion or molecule, including all P-donor ligands, that binds to the gold(III) ion. It includes one or more than one phosphino molecules.

As used herein, the term "P-donor ligand" refers to an ion or molecule using the electron rich phosphorus atom, that binds to the gold(III) ion of the invention. It includes but not limited to one or more than one coordinating compounds such as triphenylphosphine (TPP), 1,2-bis(diphenylphosphino)methane (dppm), 1,2-bis(diphenylphosphino)ethane (dppe), 1,2-bis(diphenylphosphino)propane (dppp), 1,2-bis(diphenylphosphino)butane (dppb), 1,2-bis(diphenylphosphino)pentane (dpppe), 1,2-bis(diphenylphosphino)hexane (dpph), or bis(diphenylphosphinoethyl) Phenylphosphine (dpep).

In structural formulas I and II, $R^1$-$R^{15}$ are each independently hydrogen, alkyl, substituted alkyl, alkenyl, substituted alkenyl, alkynyl, substituted alkynyl, phenyl, substituted phenyl, halo, nitro, hydroxyl, alkoxyl, substituted alkoxyl, phenoxyl, substituted phenoxyl, aroxyl, substituted aroxyl, alkylthio, substituted alkylthio, phenylthio, substituted phenylthio, cyano, isocyano, substituted isocyano, carbonyl, substituted carbonyl, carboxyl, substituted carboxyl, amino, substituted amino, amido, substituted amido, sulfinyl, substituted sulfinyl, sulfonyl, substituted sulfonyl, sulfonic acid, substituted sulfonic acid, phosphonato, substituted phosphonato, phosphoramide, substituted phosphoramide, $C_1$-$C_{20}$ cyclic, substituted $C_1$-$C_{20}$ cyclic, heterocyclic, substituted heterocyclic, amino acid, peptide, or polypeptide group.

In one embodiment, the method relates to the induction of cancer cell death by administering to a patient in need thereof a composition comprising an effective amount of an $[Au^{III}_m(CNC)_mL]^{n+}$ complex of formula I or a pharmaceutically acceptable salt thereof, wherein $R^1$-$R^{11}$ are each —H; m is 1; n is 0; $qX^p$ is absent; and L is:

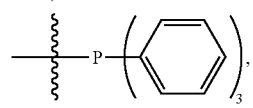

(3a)

and a pharmaceutically acceptable carrier.

In yet another embodiment, the method for the induction of cancer cell death is by administering to a patient in need thereof a composition comprising an effective amount of a $[Au^{III}{}_m(CNC)_mL]^{n+}$ complex of formula I or a pharmaceutically acceptable salt thereof, wherein $R^1$-$R^{11}$ are each —H; m is 1; n is 0; $qX^p$ is absent; and L is:

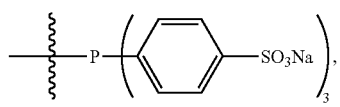

(3ai)

and a pharmaceutically acceptable carrier.

In a further embodiment, the method for the induction of cancer cell death is by administering to a patient in need thereof a composition comprising an effective amount of a $[Au^{III}{}_m(CNC)_mL]^{n+}$ complex of formula I or a pharmaceutically acceptable salt thereof wherein $R^1$-$R^{11}$ are each —H; m is 2; n is 2; q is 2; $X^p$ is $CF_3SO_3^-$; and L is:

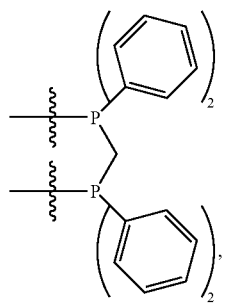

(3b)

and a pharmaceutically acceptable carrier.

In another embodiment, the method for the induction of cancer cell death is by administering to a patient in need thereof a composition comprising an effective amount of a $[Au^{III}{}_m(CNC)_mL]^{n+}$ complex of formula I or a pharmaceutically acceptable salt thereof, wherein $R^1$-$R^{11}$ are each —H; m is 2; n is 2; q is 2; $X^p$ is $CF_3SO_3^-$; and L is:

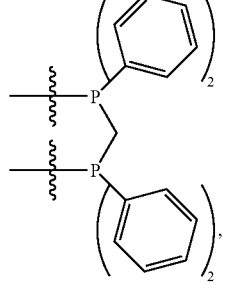

(3c)

and a pharmaceutically acceptable carrier.

In another embodiment, the method for the induction of cancer cell death is by administering to a patient in need thereof a composition comprising an effective amount of a $[Au^{III}{}_m(CNC)_mL]^{n+}$ complex of formula I or a pharmaceutically acceptable salt thereof, wherein $R^1$-$R^{11}$ are each —H; m is 2; n is 2; q is 2; $X^p$ is $CF_3SO_3^-$; and L is:

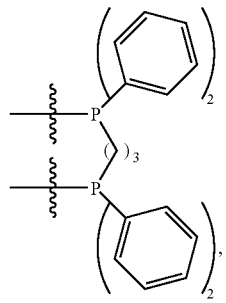

(3d)

and a pharmaceutically acceptable carrier.

In another embodiment, the method for the induction of cancer cell death is by administering to a patient in need thereof a composition comprising an effective amount of a $[Au^{III}{}_m(CNC)_mL]^{n+}$ complex of formula I or a pharmaceutically acceptable salt thereof, wherein $R^1$-$R^{11}$ are each —H; m is 2; n is 2; q is 2; $X^p$ is $CF_3SO_3^-$; and L is:

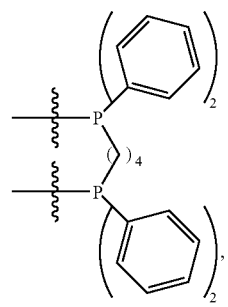

(3e)

and a pharmaceutically acceptable carrier.

In another embodiment, the method for the induction of cancer cell death is by administering to a patient in need thereof a composition comprising an effective amount of a $[Au^{III}{}_m(CNC)_mL]^{n+}$ complex of formula I or a pharmaceutically acceptable salt thereof wherein $R^1$-$R^{11}$ are each —H; m is 2; n is 2; q is 2; $X^p$ is $CF_3SO_3^-$; and L is:

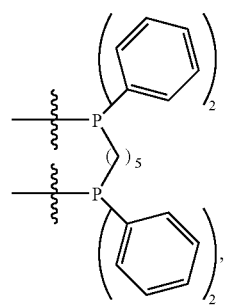

(3f)

and a pharmaceutically acceptable carrier.

In another embodiment, the method for the induction of cancer cell death is by administering to a patient in need thereof a composition comprising an effective amount of a $[Au^{III}{}_m(CNC)_mL]^{n+}$ complex of formula I or a pharmaceutically acceptable salt thereof, wherein $R^1$-$R^{11}$ are each —H; m is 2; n is 2; q is 2; $X^p$ is $CF_3SO_3^-$; and L is:

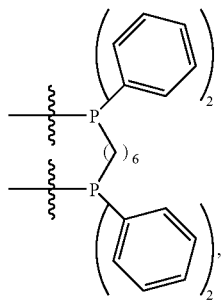
(3g)

and a pharmaceutically acceptable carrier.

In another embodiment, the method for the induction of cancer cell death is by administering to a patient in need thereof a composition comprising an effective amount of a $[Au^{III}_m(CNC)_mL]^{n+}$ complex of formula I or a pharmaceutically acceptable salt thereof, wherein $R^1$-$R^{11}$ are each —H; m is 3; n is 3; q is 3; $X^p$ is $CF_3SO_3^-$; and L is:

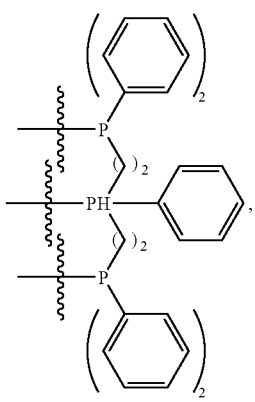
(3h)

and a pharmaceutically acceptable carrier.

In another embodiment, the method for the induction of cancer cell death is by administering to a patient in need thereof a composition comprising an effective amount of a $[Au^{III}_m(CNC)_mL]^{n+}$ complex of formula II or a pharmaceutically acceptable salt thereof, wherein $R^1$-$R^{15}$ are each —H; m is 1; n is 0; $qX^p$ is absent; and L is:

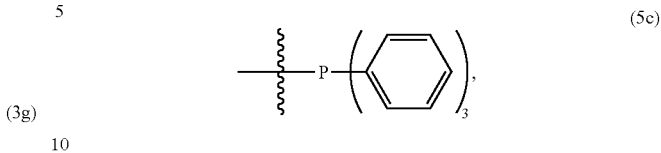
(5c)

and a pharmaceutically acceptable carrier.

In another embodiment, the method for the induction of cancer cell death is by administering to a patient in need thereof a composition comprising an effective amount of a $[Au^{III}_m(CNC)_mL]^{n+}$ complex of formula II or a pharmaceutically acceptable salt thereof, wherein $R^1$-$R^{15}$ are each —H; m is 1; n is 0; $qX^p$ is absent; and L is:

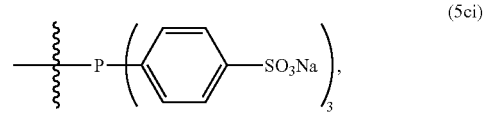
(5ci)

and a pharmaceutically acceptable carrier.

In another embodiment, the method for the induction of cancer cell death is by administering to a patient in need thereof a composition comprising an effective amount of a $[Au^{III}_m(CNC)_mL]^{n+}$ complex of formula II or a pharmaceutically acceptable salt thereof, wherein $R^1$-$R^{15}$ are each —H; m is 2; n is 2; q is 2; $X^p$ is $CF_3SO_3^-$; and L is:

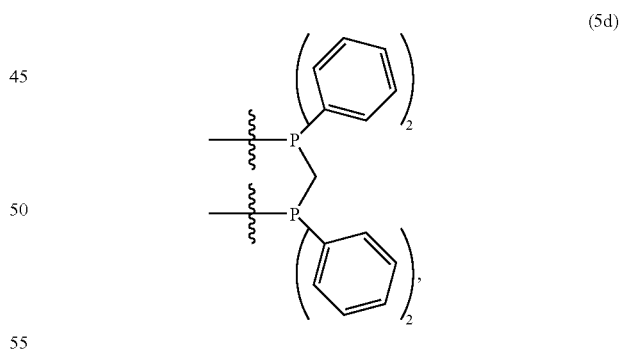
(5d)

and a pharmaceutically acceptable carrier.

In another embodiment, the method for the induction of cancer cell death is by administering to a patient in need thereof a composition comprising an effective amount of a $[Au^{III}_m(CNC)_mL]^{n+}$ complex of formula II or a pharmaceutically acceptable salt thereof, wherein $R^1$-$R^{11}$ are each —H; m is 2; n is 2; q is 2; $X^p$ is $CF_3SO_3^-$; and L is:

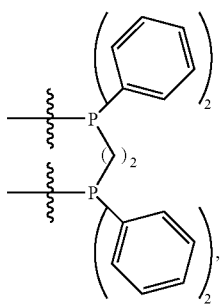

(5e)

and a pharmaceutically acceptable carrier.

In another embodiment, the method for the induction of cancer cell death is by administering to a patient in need thereof a composition comprising an effective amount of a $[Au^{III}_m(CNC)_mL]^{n+}$ complex of formula II or a pharmaceutically acceptable salt thereof wherein $R^1$-$R^{15}$ are each —H; m is 3; n is 3; q is 3; $X^p$ is $CF_3SO_3^-$; and L is:

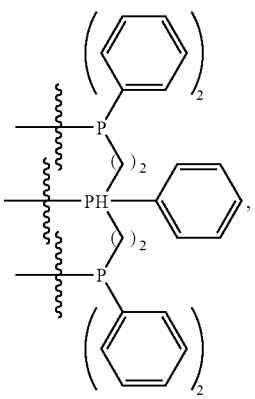

(5f)

and a pharmaceutically acceptable carrier.

In another embodiment, the method for the inhibition of tumor growth in an orthotopic rat hepatocellular carcinoma model using the rat hepatoma cells McA-RH7777, is by administering to a patient in need thereof an effective amount of the $[Au^{III}_m(CNC)_mL]^{n+}$ complexes of formula I and II or a pharmaceutically acceptable salt.

Compounds designated 3d, 3e, 3f, 3g, 3h, 5c, 5d, 5e and 5f have not previously been described in the literature: 2,6-diphenylpyridine—gold co-ordination complexes of formula I:

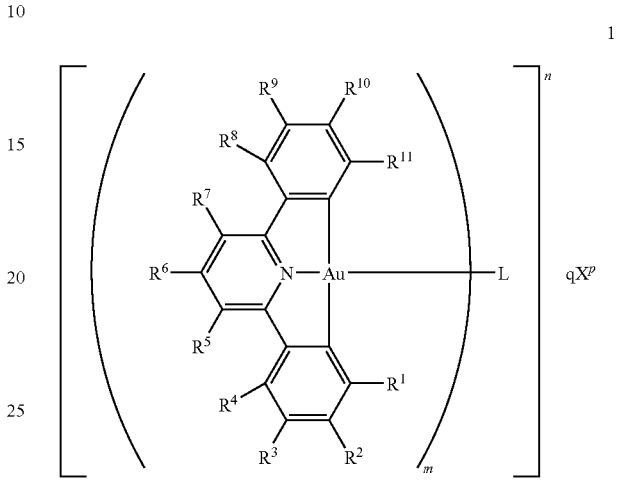

1 wherein each of $R^1$-$R^{11}$ is H, m is 2, n is 0, qX is absent or is a pharmaceutically acceptable counter-ion such as trifluoromethylsulfonate, and L is a 1,2-bis(diphenylphosphino) $C^3$-$C^6$ alkane group.

Of particular interest, and therefore constituting a specific preferred embodiment is the compound of the above formula in which the group L is 1,2-bis(diphenylphosphino)propane, compound 3d in the specific examples which follow. This compound has been found to have a potency against cancers which is about 200 times greater than that of the clinically used cis-platin. It is, in addition, highly active toward hepatocellular carcinoma, for which the mortality rate in human patients is high. It can be taken orally, and intestinally absorbed Moreover, in vivo toxicity studies have revealed that this compound is non-toxic to nude mice even at concentrations 20-fold higher than the effective dose, and does not cause DNA mutation upon usage.

Scheme 1 shows illustrative examples of the $[Au^{III}_m(CNC)_mL]^{n+}$ complexes.

Scheme 1

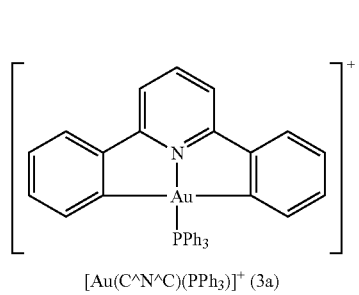

[Au(C^N^C)(PPh3)]$^+$ (3a)

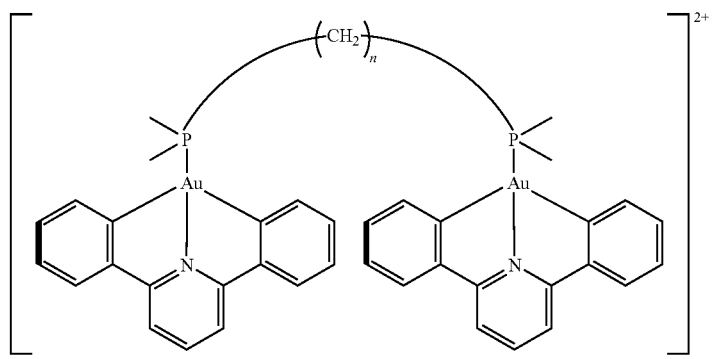

-continued

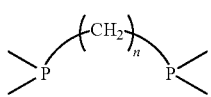
= 1,2-bis(diphenylphosphino)methane, [Au$_2$(C^N^C)$_2$(μ-dppm)]$^{2+}$ (3b)
= 1,2-bis(diphenylphosphino)ethane, [Au$_2$(C^N^C)$_2$(μ-dppe)]$^{2+}$ (3c)
= 1,2-bis(diphenylphosphino)propane, [Au$_2$(C^N^C)$_2$(μ-dppp)]$^{2+}$ (3d)
= 1,2-bis(diphenylphosphino)butane, [Au$_2$(C^N^C)$_2$(μ-dppb)]$^{2+}$ (3e)
= 1,2-bis(diphenylphosphino)pentane, [Au$_2$(C^N^C)$_2$(μ-dpppe)]$^{2+}$ (3f)
= 1,2-bis(diphenylphosphino)hexane, [Au$_2$(C^N^C)$_2$(μ-dpph)]$^{2+}$ (3g)

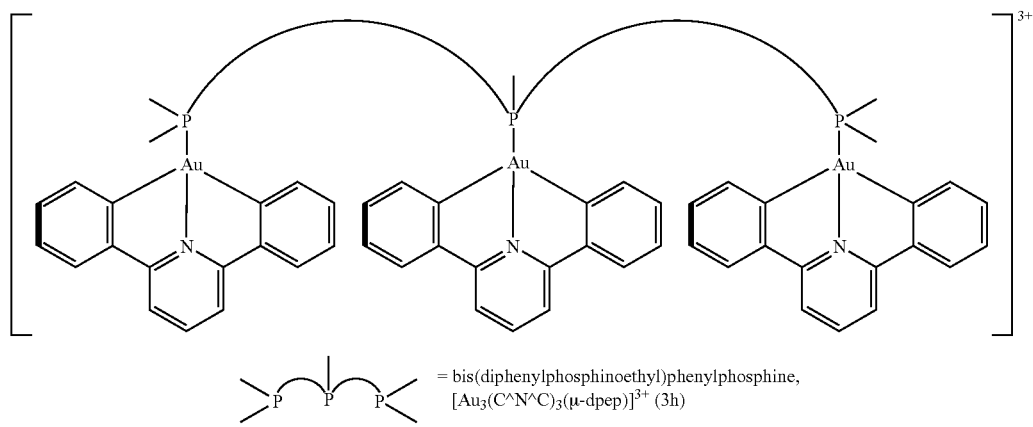

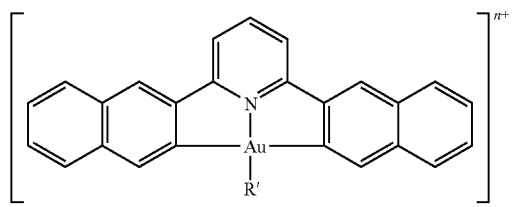
= bis(diphenylphosphinoethyl)phenylphosphine, [Au$_3$(C^N^C)$_3$(μ-dpep)]$^{3+}$ (3h)

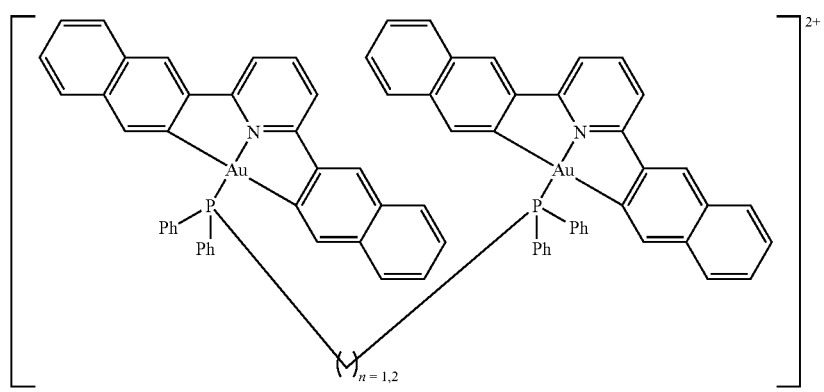

R' = PPh$_3$, n = 1, [Au(Np-C^N^C)(PPh$_3$)]$^+$ (5c)

n = 1, [Au$_2$(Np-C^N^C)$_2$(μ-dppm)]$^{2+}$ (5d)
n = 2, [Au$_2$(Np-C^N^C)$_2$(μ-dppe)]$^{2+}$ (5e)

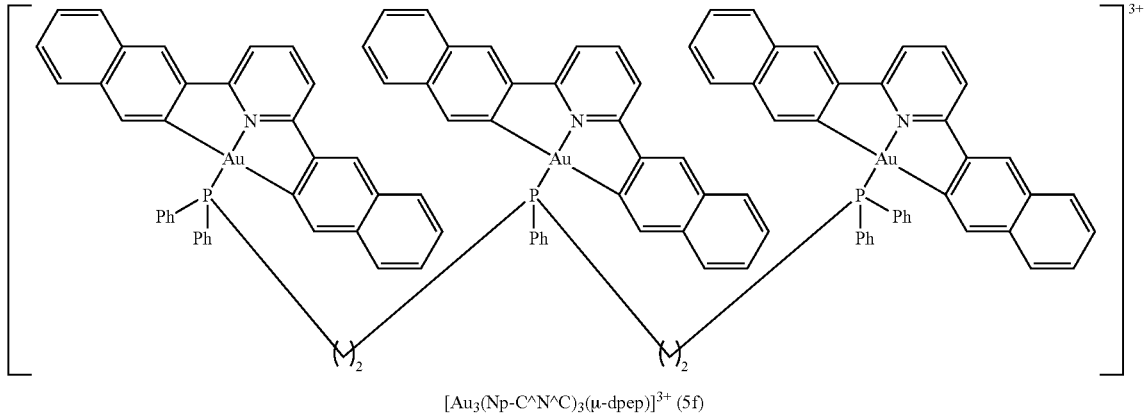

[Au₃(Np-C^N^C)₃(μ-dpep)]³⁺ (5f)

EXAMPLES

Example 1

Preparation and Characterization of the Gold(III) Complexes

In general, $[Au^{III}{}_m(CNC)_mL]^{n+}$ complexes can be synthesized by reacting $K[Au^{III}Cl_4]$ with desired CNC ligand under refluxing condition as reported in literature [V. W.-W. Yam, K. M.-C. Wong, L.-L. Hung, N. Zhu, *Angew. Chem. Int. Ed. Engl.* 2005, 44, 3107].

The syntheses and characterization of 3a-c had been reported previously [K.-H. Wong, K.-K. Cheung, M. C.-W. Chan, C.-M. Che, *Organometallics* 1998, 17, 3505].

Analytical data for the $[Au^{III}{}_m(CNC)_mL]^{n+}$ complexes are shown below:

[Au₂(CNC)₂(μ-dppp)](CF₃SO₃)₂ (3d(CF₃SO₃)₂). The procedure was similar to that for 3b except 1,2-bis(diphenylphosphino)propane (dppp) was used. Yield; 59%; Calcd for C₆₃H₄₈F₆N₂O₆P₂S₂Au₂: C, 48.41; H, 3.10; N, 1.79. Found: C, 48.22; H, 3.08; N, 1.95. ¹H NMR (300 MHz, [D₆] DMSO): δ=8.21 (t, J=8.0 Hz, 2H), 7.94-7.88 (m, 12H), 7.61-7.46 (m, 16H), 6.91 (t, J=7.3 Hz, 4H), 6.50 (t, J=7.4 Hz, 4H), 6.10 (d, J=7.5 Hz, 4H), 3.78 (s, 4H), 3.47 ppm (s, 2H); UV/Vis (DMSO): λ$_{max}$/nm (log ε) 264 (4.68), 308 (4.23, sh), 389 (3.81), 403 (3.78); FAB-MS: m/z: 1414 [M⁺].

[Au₂(CNC)₂(μ-dppb)](CF₃SO₃)₂ (3e(CF₃SO₃)₂). The procedure was similar to that for 3b except 1,2-bis(diphenylphosphino)butane (dppb) was used. Yield: 44%; Calcd for C₆₄H₅₀F₆N₂O₆P₂S₂Au₂: C, 48.74; H, 3.20; N, 1.78. Found: C, 49.47; H, 3.31; N, 1.77. ¹H NMR (400 MHz, [D₆] DMSO): δ=8.22 (t, J=8.0 Hz, 2H), 7.96-7.93 (m, 12H), 7.75 (d, J=7.8 Hz, 4H), 7.56-7.46 (m, 12H), 7.07 (t, J=74 Hz, 4H), 6.69 (t, J=7.3 Hz, 4H), 6.21 ppm (d, J=7.6 Hz, 4H); UV/Vis (DMSO): λ$_{max}$/nm (log ε) 261 (4.73), 308 (4.21, sh), 387 (3.72), 402 (3.68); FAB-MS: m/z: 1428 [M⁺].

[Au₂(CNC)₂(μ-dpppe)](CF₃SO₃)₂ (3f(CF₃SO₃)₂). The procedure was similar to that for 3b except 1,2-bis(diphenylphosphino)pentane (dpppe) was used. Yield: 47%; Calcd for C₆₅H₅₂F₆N₂O₆P₂S₂Au₂: C, 49.07; H, 3.29; N, 1.76. Found: C, 48.94; H, 3.32; N, 1.78. ¹H NMR (300 MHz, [D₆] DMSO): δ=8.28 (t, J=8.0 Hz, 2H), 8.05 (dd, J=1.8, 6.1 Hz, 4H), 7.93-7.87 (m, 12H), 7.64-7.49 (m, 4H), 7.53-7.49 (m, 8H), 7.18 (t, J=7.4 Hz, 4H), 6.83 (t, J=7.8 Hz, 4H), 6.26 (d, J=6.9 Hz, 4H), 2.06 (d, J=3.9 Hz, 2H), 1.78 ppm (s, 8H); UV/Vis (DMSO): λ$_{max}$/nm (log ε) 262 (4.78), 280 (4.52, sh), 308 (4.29, sh), 385 (3.83), 403 (3.80); FAB-MS: m/z: 1441 [M⁺].

[Au₂(CNC)₂(μ-dpph)](CF₃SO₃)₂ (3g(CF₃SO₃)₂). The procedure was similar to that for 3b except 1,2-bis(diphenylphosphino)hexane (dpph) was used. Yield: 47%; Calcd for C₆₆H₅₄F₆N₂O₆P₂S₂Au₂: C, 49.39; H, 3.39; N, 1.75. Found: C, 50.26; H, 3.54; N, 1.82. ¹H NMR (300 MHz, [D₆] DMSO): δ=8.28 (t, J=8.0 Hz, 2H), 8.05 (dd, J=1.9, 6.2 Hz, 4H), 7.99-7.91 (m, 12H), 7.64-7.48 (m, 12H), 7.20 (t, J=7.4 Hz, 4H), 6.85 (t, J=7.5 Hz, 4H), 6.28 ppm (d, J=7.7 Hz, 4H); UV/Vis (DMSO): λ$_{max}$/nm (log ε) 261 (4.86), 282 (4.54), 307 (4.32), 387 (3.85), 402 (3.82); FAB-MS: m/z: 1455 [M⁺].

[Au₃(CNC)₃(μ-dpep)](CF₃SO₃)₃ (3h(CF₃SO₃)₃). The procedure was similar to that for 3b except bis(diphenylphosphinoethyl)phenylphosphine (dpep) was used. Yield: 46%; Calcd for C₈₈H₆₆F₉N₃O₉P₃S₃Au₃: C, 46.76; H, 2.94; N, 1.86. Found: C, 46.44; H, 3.00; N, 1.80. ¹H NMR (500 MHz, [D₆] DMSO): δ=8.07-8.02 (m, 3H), 7.91 (dd, J=7.3, 5.7 Hz, 2H), 7.65-7.32 (m, 35H), 7.03 (t, J=7.6 Hz, 4H), 6.89 (t, J=7.5 Hz, 2H), 6.57 (br, 2H), 6.51 (t, J=7.5 Hz, 4H), 6.33 (s, 2H), 6.04 (d, J=7.6 Hz, 4H), 3.82-3.74 (m, 2H), 3.71-3.61 (m, 2H), 3.46-3.36 (m, 2H), 3.29-3.19 ppm (m, 2H); UV/Vis (DMSO): λ$_{max}$/nm (log ε) 266 (4.75), 308 (4.42, sh), 392 (3.92), 403 (3.91); FAB-MS: m/z: 2111 [M⁺].

[Au(Np-CNC)(PPh₃)](CF₃SO₃) (5c(CF₃SO₃)). The procedure was similar to that for 5b except triphenylphosphine (PPh₃) was used. Yield: 78%; Anal. Calcd for C₄₄H₃₀F₃NO₃PSAu: C, 56.36; H, 3.22; N, 1.49. Found: 56.21; H, 3.26; N, 1.50. ¹H NMR (400 MHz, DMF-d₇): δ=6.65 (s, 2H), 7.04 (d, J=8.0 Hz, 2H), 7.44 (t, J=8.1 Hz, 2H), 7.51 (t, J=8.1 Hz, 2H), 7.79 (td, J=7.7, 3.0 Hz, 6H), 7.91 (t, J=7.4 Hz, 3H), 7.94 (d, J=8.0 Hz, 2H), 8.28 (dd, J=7.7, 13.5 Hz, 6H), 8.53 (m, 3H), 8.77 ppm (s, 2H); ³¹P NMR (162 MHz, CD₃CN): δ=39.02 ppm; UV/Vis (DMSO): λ$_{max}$/nm (log ε) 280 (4.84), 298 (4.71, sh), 401 (4.38); FAB-MS: m/z: 788 [M⁺].

[Au₂(Np-CNC)₂(μ-dppm)](CF₃SO₃)₂ (5d(CF₃SO₃)₂). The procedure was similar to that for 5b except 1,2-bis(diphenylphosphino)methane (dppm) was used. Yield: 80%; Anal. Calcd for C₇₇H₅₂F₆N₂O₆P₂S₂Au₂: C, 53.30; H, 3.02; N, 1.61. Found: C, 53.38; H, 3.05; N, 1.60. ¹H NMR (400 MHz, CD₃CN): δ=3.45 (t, J=7.2 Hz, J=7.2 Hz, 2H), 6.33 (d, J=8.0 Hz, 4H), 6.61 (s, 4H), 7.12 (t J=8.0 Hz, 4H), 7.24 (t, J=8.0 Hz, 4H), 7.34 (br, 12H), 7.38 (d, J=8.0 Hz, 4H), 7.43 (d, J=8.0 Hz, 4H), 7.58 (s, 4H), 7.80 (t, J=8.0 Hz, 2H), 8.26 ppm (br, 8H);

$^{31}$P NMR (162 MHz, CD$_3$CN): δ=23.89 ppm; UV/Vis (DMSO): λ$_{max}$/nm (log ε) 258 (5.01), 276 (5.01), 396 (4.41); FAB-MS: m/z: 1437 [M$^+$].

[Au$_2$(Np-CNC)$_2$(μ-dppe)](CF$_3$SO$_3$)$_2$ (5e(CF$_3$SO$_3$)$_2$). The procedure was similar to that for 5b except 1,2-bis(diphenylphosphino)ethane (dppe) was used. Yield: 75%; Anal. Calcd for C$_{78}$H$_{54}$F$_6$N$_2$O$_6$P$_2$S$_2$Au$_2$: C, 53.56; H, 3.11; N, 1.60. Found: C, 53.65; H, 3.10; N, 1.62. $^1$H NMR (400 MHz, CD$_3$CN): δ=4.57 (s, 4H), 6.45 (d, J=8.0 Hz, 4H), 6.49 (s, 4H), 7.20 (t, J=7.9 Hz, 4H), 7.43-7.49 (m, 16H), 7.58 (t, J=7.5 Hz, 4H), 7.69 (t, J=8.1 Hz, 4H), 7.75 (s, 4H), 7.96 (t, J=8.0 Hz, 2H), 8.07 ppm (dd, J=13.3, 7.2 Hz, 8H); $^{31}$P NMR (162 MHz, CD$_3$CN): δ=34.97 ppm; UV/Vis (DMSO): λ$_{max}$/nm (log δ) 261 (5.01), 277 (5.03), 403 (4.46); FAB-MS: m/z: 1600 [M$^+$+ OTf], 1451 [M$^+$].

[Au$_3$(Np-CNC)$_3$(μ-dpep)](CF$_3$SO$_3$)$_3$ (5f(CF$_3$SO$_3$)$_3$). The procedure was similar to that for 5b except 1,2-bis(diphenylphosphinoethyl)phenylphosphine (dpep) was used. Yield: 78%; Anal. Calcd for C$_{112}$H$_{78}$F$_9$N$_3$O$_9$P$_3$S$_3$Au$_3$: C, 52.53; H, 3.07; N, 1.64. Found: C, 52.58; H, 3.02; N, 1.59. $^{31}$P NMR (162 MHz, CD$_3$CN): δ=33.22 (d, J=50.2 Hz), 36.83 ppm (t, J=50.3 Hz); UV/Vis (DMSO): λ$_{max}$/nm (log ε) 259 (5.21), 277 (5.24), 406 (4.74); FAB-MS: m/z: 2412 [M$^+$+2OTf], 2263 [M$^+$+OTf], 2113 [M$^+$].

X-ray crystal structure determination. X-ray crystal structures of 3d(CF$_3$SO$_3$)$_2$.4CH$_3$CN, 3h(CF$_3$SO$_3$)$_3$.CH$_3$CN.H$_2$O, 5c(CF$_3$SO$_3$).CHCl$_3$, 5d(CF$_3$SO$_3$)$_2$.H$_2$O, 5e(CF$_3$SO$_3$)$_2$.2Et$_2$O, and 5f(CF$_3$SO$_3$)$_3$.6CHCl$_3$.H$_2$O are shown in FIG. 1. Compounds 3d(CF$_3$SO$_3$)$_2$.4CH$_3$CN and 3h(CF$_3$SO$_3$)$_3$.CH$_3$CN.H$_2$O were grown by slow diffusion of Et$_2$O into CH$_3$CN solution; 5c(CF$_3$SO$_3$).CHCl$_3$, 5d(CF$_3$SO$_3$)$_2$.H$_2$O, 5e(CF$_3$SO$_3$)$_2$.2Et$_2$O, and 5f(CF$_3$SO$_3$)$_3$.6CHCl$_3$.H$_2$O were grown by slow diffusion of Et$_2$O into CHCl$_3$ solution.

Example 2

Stability Studies of the Gold(III) Complexes

Example 2 describes the results of stability studies for illustrative gold(III) complexes.

All these gold(III) compounds exhibit a vibronic structure absorption band with peak maxima at 304-318 nm in DMSO. At a concentration of 50 μM, all compounds exhibited excellent stability in organic solvents, as no significant UV-vis spectral changes were observed over a 24-h period at room temperature. The electrochemical properties of the gold(III) compounds in DMF were studied by cyclic voltammetry. As compared to KAuCl$_4$ [E°$_{gold(III) \rightarrow gold(I)}$=−0.4 V], the substantially more cathodic potentials of −1.43 to −1.83 V vs Cp$_2$Fe$^{+/0}$ required for the gold(III) reduction in all the gold (III) compounds is consistent with stabilization of gold(III) by the dianionic CNC ligand. Thus, it is not surprising to find that these gold(III) compounds are not easily reduced under physiological conditions. Treatment of the gold(III) compounds with glutathione (GSH, 2 mM) in Tris buffered saline (TBS)-DMSO (9:1) solution did not result in any significant UV-vis spectral changes over a 24-h period. In addition, there were no UV-vis, $^{31}$P or $^1$H NMR spectral changes (FIG. 2) observed for 3d (as example of phosphine-containing gold (iii) compound) upon standing in DMSO or TBS for 24 h. This demonstrated that these gold(III) compounds are stable in solution.

Example 3

Cytotoxicity Studies of the Gold(III) Complexes Towards Different Cancer and Normal Cell Lines DNA is a major target for anticancer drugs [L. H. Harley, Nature Rev. Cancer 2002, 2, 188], and the binding of gold(III) compounds to DNA has been studied extensively. The binding affinities of the phosphino-containing 3a and 3d compounds to calf thymus DNA (ctDNA) were examined by means of UV-vis absorption titration. Their binding constants (K$_b$) toward ctDNA were determined from the plot of [ctDNA]/Δε$_{ap}$ vs [ctDNA] [C. V. Kumar, E. H. Asuncion, J. Am. Chem. Soc. 1993, 115, 8547], with the K$_b$ values of (2.1±0.7)×10$^4$ dm$^3$ mol$^{-1}$ and (7.1±0.7)×10$^3$ dm$^3$ mol$^{-1}$ for 3a and 3d respectively, which are comparable to that of the [Pt(terpy)L]$^+$ compounds.

Compound 3d does not intercalate double-stranded DNA. A gel mobility shift assay was employed to determine the intercalating property 3d [E. C. Long, J. K. Barton, Acc. Chem. Res. 1990, 23, 271] to evaluate the effect 3d, had upon the DNA binding affinities. A 100-base pair DNA ladder treated with 3d, or ethidium bromide (EB, DNA intercalator) as well as a control were resolved by agarose gel electrophoresis. Briefly, gel electrophoresis of 100-bp DNA ladder on a 1.5% (w/v) agarose gel was performed showing the mobility of DNA (50 μM bp-1) in the absence or presence of ethidium bromide (EB), or compound 3d. Only EB exhibited a tailing effect, which is due to the intercalation of this complex to the DNA, since the binding would cause elongation of DNA. The bound DNA would have lower mobility compared to that of the free DNA. In contrast, 3d did not cause this tailing effect indicating that this compound does not bind to DNA by intercalation.

Example 4

Cytotoxicity Studies of the Gold(III) Complexes Towards Different Cancer and Normal Cell Lines Example 4 describes the results of in vitro cytotoxicity studies of the gold(III)-phosphino complexes.

The cytotoxicities of the gold(III) compounds toward several human cancer cell lines including nasopharyngeal carcinoma (SUNE1, and its cisplatin variant CNE1), hepatocellular carcinoma (HepG2), and cervical epitheloid carcinoma (HeLa) were determined using a well-established MTT assay. The results are listed in Table 1.

Cisplatin chemotherapy is currently the last-line treatment for several types of cancer including nasopharyngeal carcinoma (NPC). However, resistance to cisplatin is frequently encountered. Thus, new anti-cancer agents that are active against cisplatin-resistant cell lines are in obvious need. As shown in Table 1, the gold(III) compounds are equally cytotoxic toward the cisplatin-sensitive and -resistant NPC (SUNE1 and CNE1, respectively). The resistance factor, IC$_{50}$ (CNE1/SUNE1), for cisplatin is 3.3, whereas the corresponding values for the gold(III) compounds are close to unity (Table 1). The lack of cross resistance suggests that the gold (III) compounds and cisplatin may induce cytotoxicity via different mechanisms, or the gold(III) compounds may bypass the cellular sequestration mechanism for cytotoxic agents (e.g. stable in elevated level of GSH).

Phosphine-containing compounds have long been known as potential anti-cancer agents. However, their instability under physiological conditions (e.g. formation of phosphine oxide) and non-specific binding affinities toward various biomolecules have hindered their clinical development as anti-cancer agents. In this work, we have found that the [Au(CNC)]+ moiety may be used as carrier for phosphino compounds.

A number of structurally distinct gold(III)-phosphino compounds (3a-g) were synthesized and assayed for cytotoxic activities against several cancer cell lines (see Table 1). All these gold(III) compounds were found to be highly cytotoxic, with $IC_{50}$ values between 0.04 and 4.3 μM. Among the gold(III)-1,2-bis(diphenylphosphino)$C_n$ analogues (where $C_n$ is a saturated hydrocarbon linker with n=1-6), 1,2-bis(diphenylphosphino)propane (dppp) tethered by two [Au(CNC)]+ units (3d) was found to be the most cytotoxic agent, with $IC_{50}$ values toward SUNE1 and HeLa cells of 0.04 and 0.05 μM, respectively. Whereas, shortening (n=1 or 2) or lengthening (n=4, 5 or 6) the hydrocarbon linker reduced the cytotoxicity, with $IC_{50}$ values increasing by at least an order of magnitude.

The $IC_{50}$ values for the metal-free 1,2-bis(diphenylphosphino)$C_n$ compounds follow a similar trend to that of the corresponding gold(III) cyclometallated compounds (3a-g), with dppp and $[Au_2(CNC)_2(\mu\text{-dppp})]^{2+}$ (3d) being the most cytotoxic metal-free and metallated agents, respectively. It appears that the cytotoxicities of these gold(III) compounds are phosphine-mediated. By means of cellular uptake experiment we found that the cytotoxicities of the phosphine-containing compounds are not solely mediated by the [Au(CNC)]+ unit. SUNE1 cells separately treated with 3a-g (50 μM, 2-h incubation) were subjected to inductively coupled plasma mass spectrometry (ICP-MS) for Au analysis. All the treated cells showed similar cellular absorption of Au which spanned over the range of 1.18-3.81 ng/cell. These cellular absorptions of Au, obviously, do not follow the trend of $IC_{50}$ values the gold(III)-1,2-bis(diphenylphosphino)$C_n$ thus revealing the presence of non-gold mediated cytotoxicity.

As mentioned earlier, ligation of the phosphine ligands to the [Au(CNC)]+ moieties improved their stabilities and aqueous solubilities. Taking its inherent cytotoxicity into consideration, our results show that [Au(CNC)]+ moiety can serve as a pendant carrier of phosphine ligands in biological systems.

Example 5

Induction of Cell-Cycle Arrest by the Gold(III) Complexes

Example 5 describes the study of cell-cycle arrest by the gold(II) complexes.

Figure 3A:
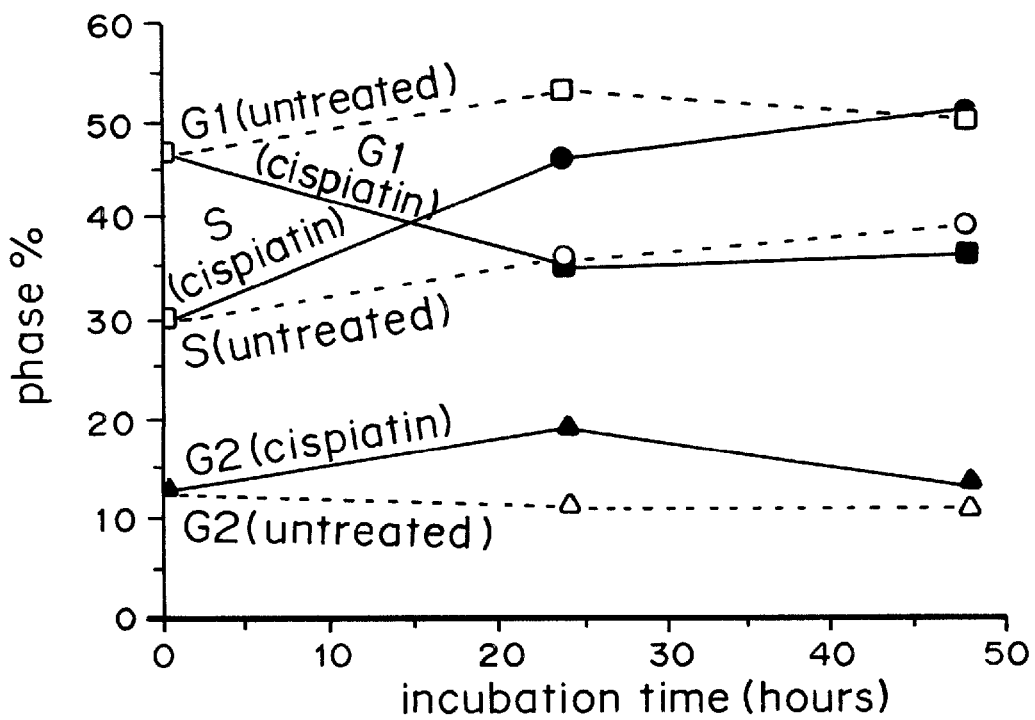
FIGS. 3A and 3B show the induction of cell-cycle arrest in the SUNE1 cells after treatment with cisplatin, and gold(III) compound 3d.
Figure 3B:
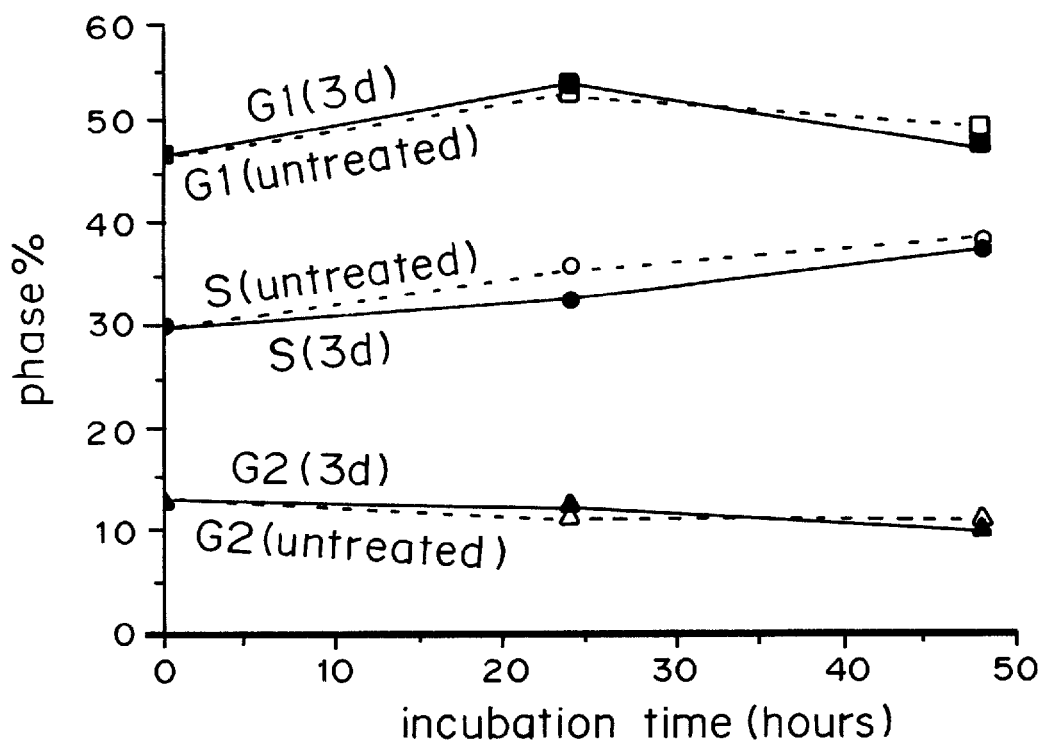
Figure 4:
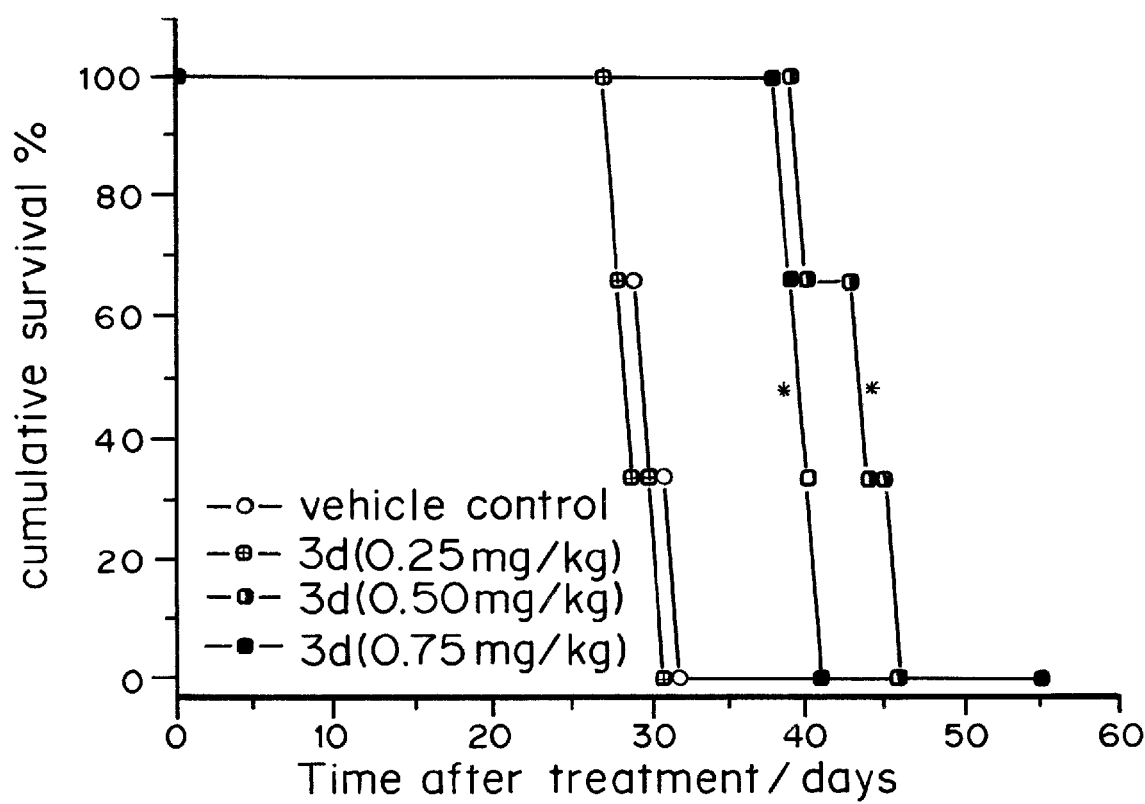

To find out whether cellular DNA is a major target of the gold(III) compounds, we studied the cell cycle profiles of 3d-treated cancer cells. Cell cycle analysis was performed by assessing the DNA content of cells stained with propidium iodide using flow cytometry. This enables quantification of the total cellular populations in the different phases of the cell cycle (G0/G1, S and G2/M). The flow cytometric data for SUNE1 cells treated with cisplatin or 3d is presented in FIGS. 3A and 3B. Treatment with 3d did not significantly affect the cell cycle after 24- or 48-h incubation. Compound 3d appears to affect its cytotoxicity via some alternative mechanistic pathways.

Example 6

In Vivo Studies of Antitumor Activity of the Gold(III) Complexes in an Orthotopic Rat Hepatocellular Carcinoma-(HCC) Model Using the Rat Hepatoma Cell McA-RH7777

Example 6 describes the in vivo anti-cancer activities of the gold(III) complexes.

The anti-tumor effect of complex 3d was examined in the rat HCC model. Male Buffalo rats, 8-12 weeks old and weighing 250-320 g, were purchased from Carles River Labs (Wilmington, Mass.). The animals were kept under standard condition with constant day-night rhythm and free access to water and standard laboratory food. Tumor model was induced by injection of $2\times10^5$ McA-RH7777 cells into the left lobe of the liver. Seven days after tumor induction, the rat livers were exposed to confirm the formation of tumor nodules. All the experimental rats had developed a single tumor nodule with size ranging from 1×2 to 2×3 mm². The animals were then divided into the following 4 groups: (1) sham operation (NT); (2) 3d, 0.25 mg/kg; (3) 3d, 0.5 mg/kg; and (4) 3d, 0.75 mg/kg. Complex 3d suspension was prepared by dissolving the complex in dimethyl sulfoxide (DMSO) and

TABLE 1

Cytotoxicities ($IC_{50}$, 72 h) of the gold(III) compounds against selected human cancer cell lines.

| compound | $IC_{50}$ (μM) | | | | $IC_{50}$ ratio |
| | HeLa[b] | HepG2[b] | SUNE1[b] | CNE1[b] | (CNE1/SUNE1) |
| --- | --- | --- | --- | --- | --- |
| 3a | n.d.[a] | n.d.[a] | 17 ± 2 | 11 ± 2 | 0.65 |
| 3b | 0.81 ± 0.08 | n.d.[a] | 0.92 ± 0.12 | 1.2 ± 0.2 | 1.3 |
| 3c | 0.14 ± 0.03 | 0.32 ± 0.08 | 0.25 ± 0.03 | 0.40 ± 0.06 | 1.6 |
| 3d | 0.043± | 0.21 ± 0.09 | 0.055± | 0.091 | 1.7 |
| 3e | 2.4 ± 0.2 | n.d.[a] | 1.5 ± 0.2 | 2.2 ± 0.3 | 1.5 |
| 3f | 1.5 ± 0.3 | n.d.[a] | 1.6 ± 0.3 | 2.5 ± 0.3 | 1.6 |
| 3g | 3.2 ± 0.4 | n.d.[a] | 4.3 ± 0.9 | 3.2 ± 0.5 | 0.74 |
| 3h | 0.93 ± 0.09 | 3.8 ± 0.6 | 0.26 ± 0.03 | 0.40 ± 0.05 | 1.5 |
| [Pt(terpy)Cl]Cl | 14 ± 2 | 23 ± 3 | 11 ± 3 | 13 ± 2 | 1.2 |
| cisplatin | 11 ± 1 | 1.6 ± 0.2 | 1.0 ± 0.1 | 3.3 ± 0.5 | 3.3 |

[a]n.d. = not determined.
[b]HeLa = human cervical epithelioid carcinoma; HepG2 = human hepatocellular carcinoma; SUNE1 = human nasopharyngeal carcinoma (cisplatin sensitive); CNE1 = human nasopharyngeal carcinoma (cisplatin resistance).

diluted with phosphate-buffered saline (pH 7.4, 1:1, v/v). Different doses of 3d (0.25, 0.5 or 0.75 mg/kg) were injected intratumorally at the first instance, followed by intraperitoneal injection twice weekly until they died.

Figures 1, 2, 3, 4, 4A:
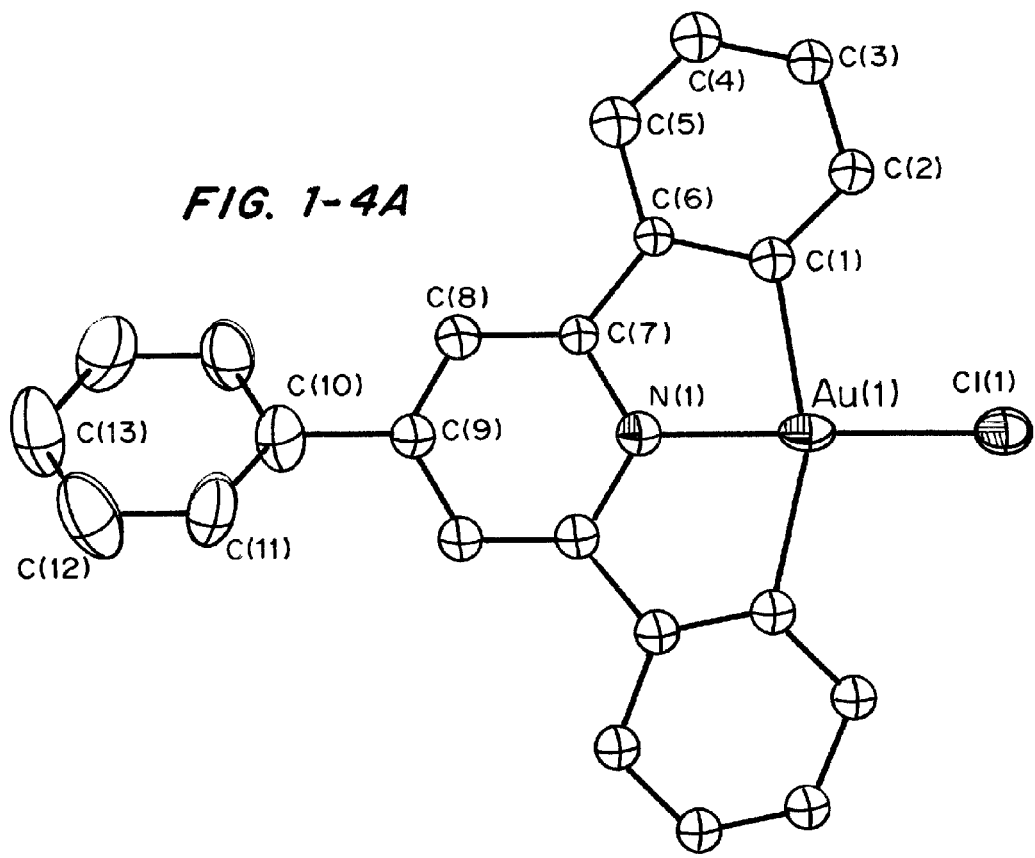
FIG. 4 shows the survival curves of HCC-bearing rats in different treatment groups. *, p<0.05, compared to the vehicle control group.
Figures 1, 2, 3, 4, 5, 5A:
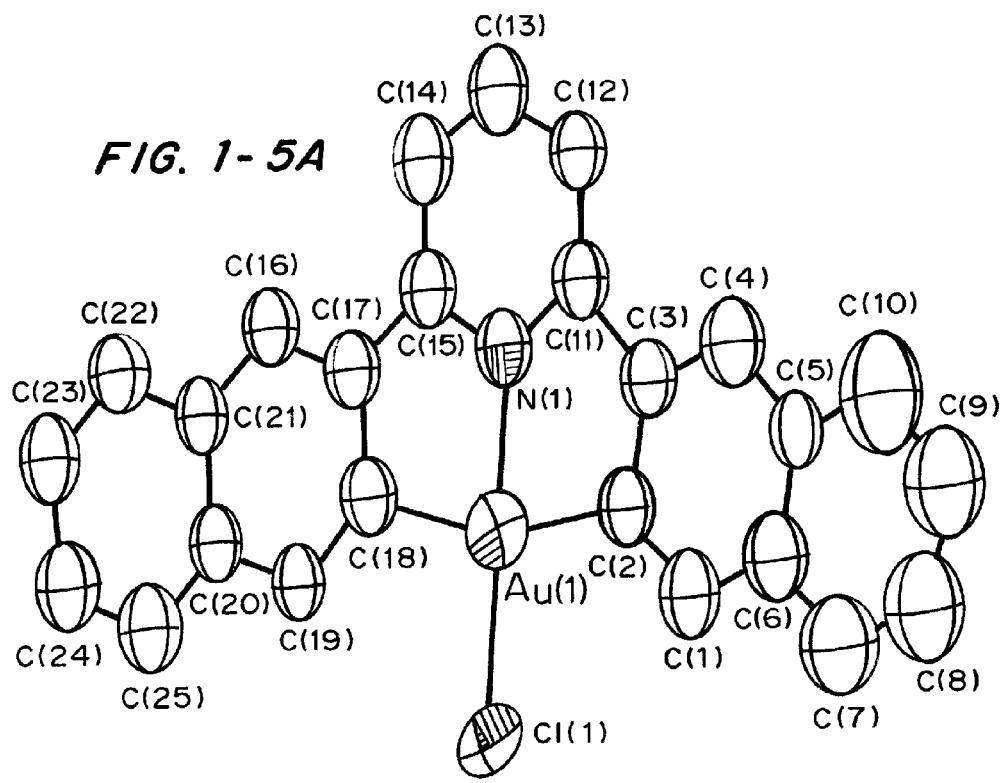
Figures 1, 2, 3, 4, 5, 5C:
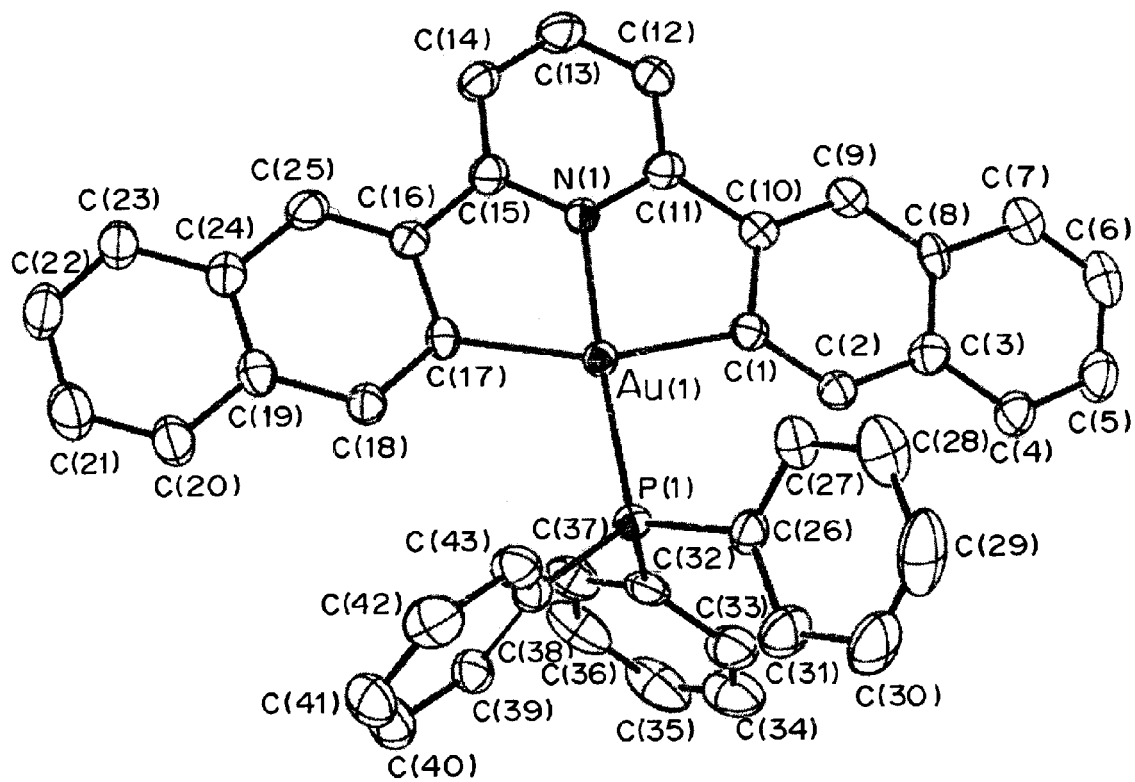
Figures 1, 2, 3, 4, 5, 5D:
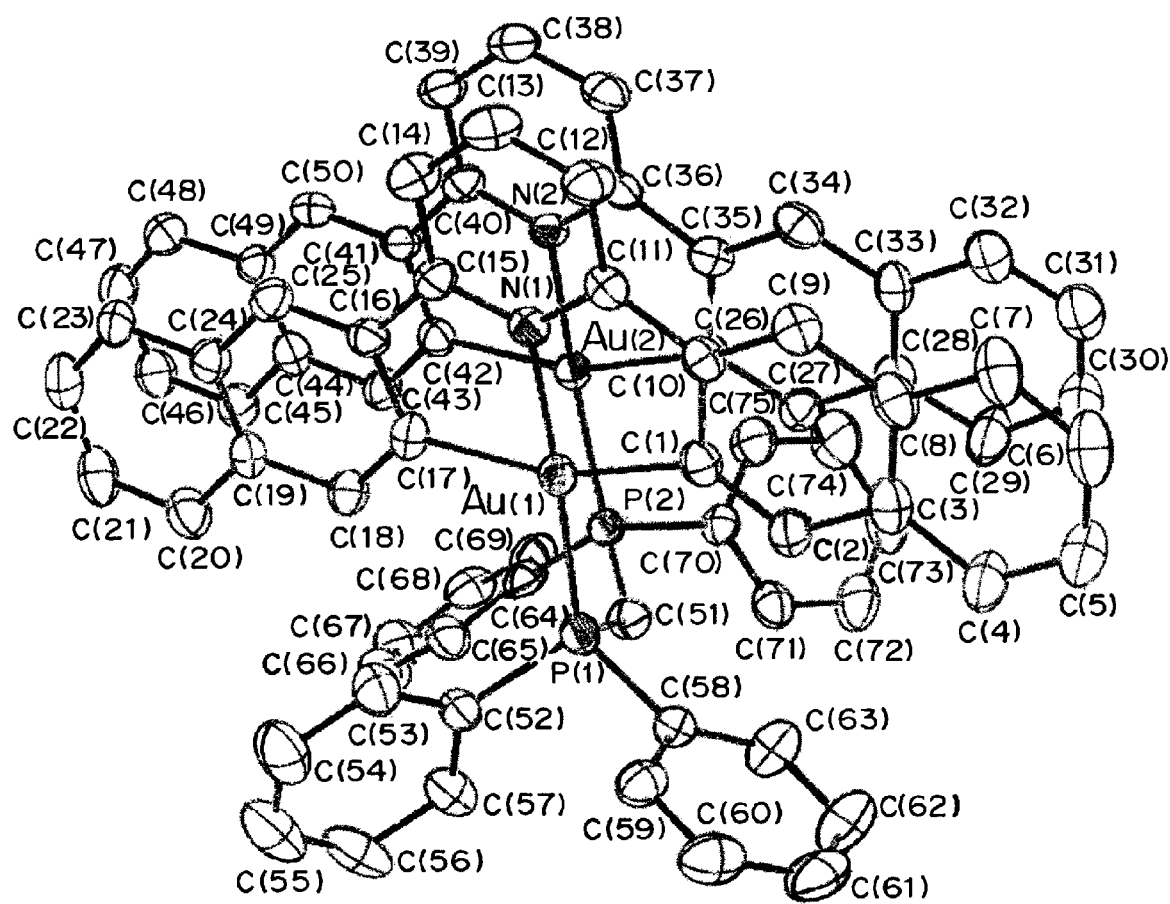
Figures 1, 2, 3, 4, 5, 5E:
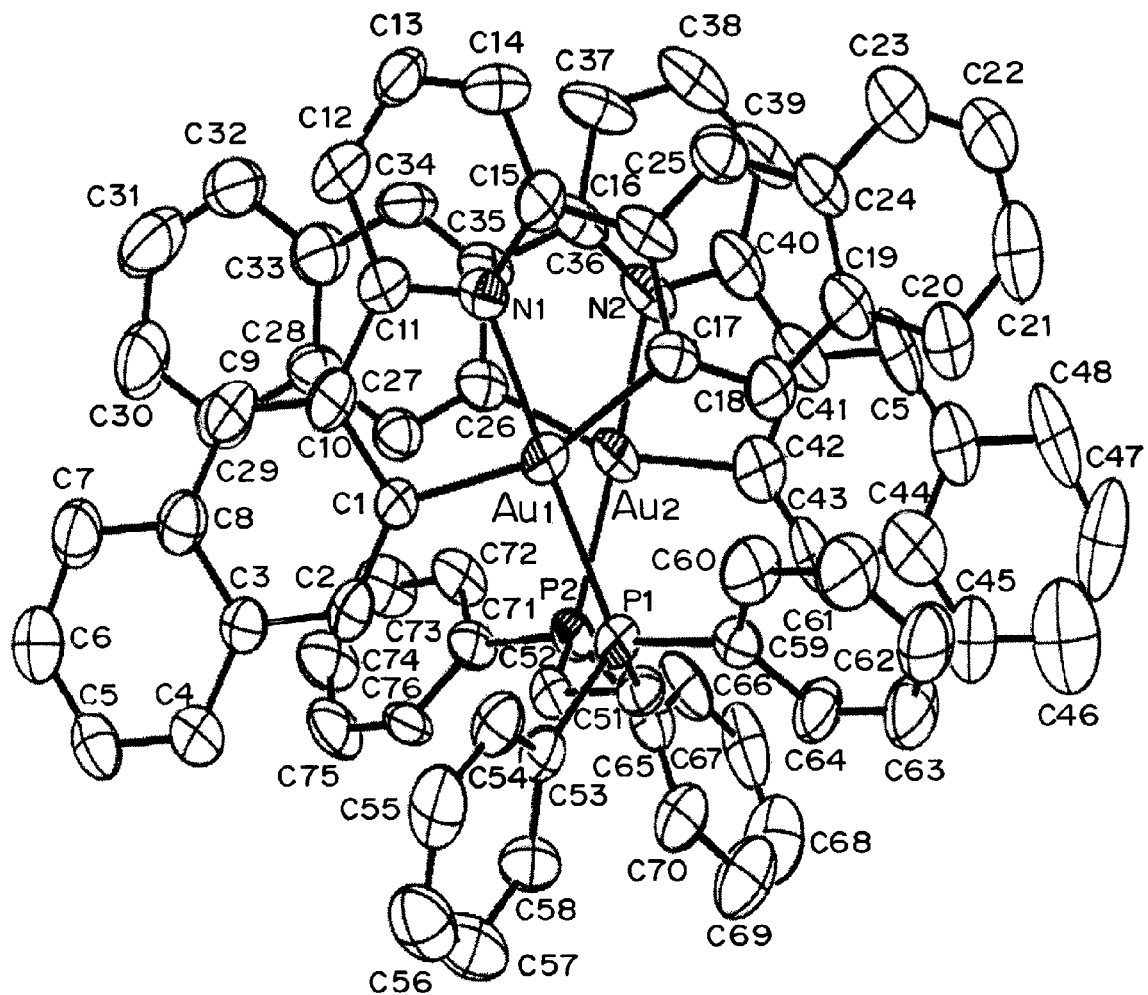
Figures 1, 2, 3, 4, 5, 5F:
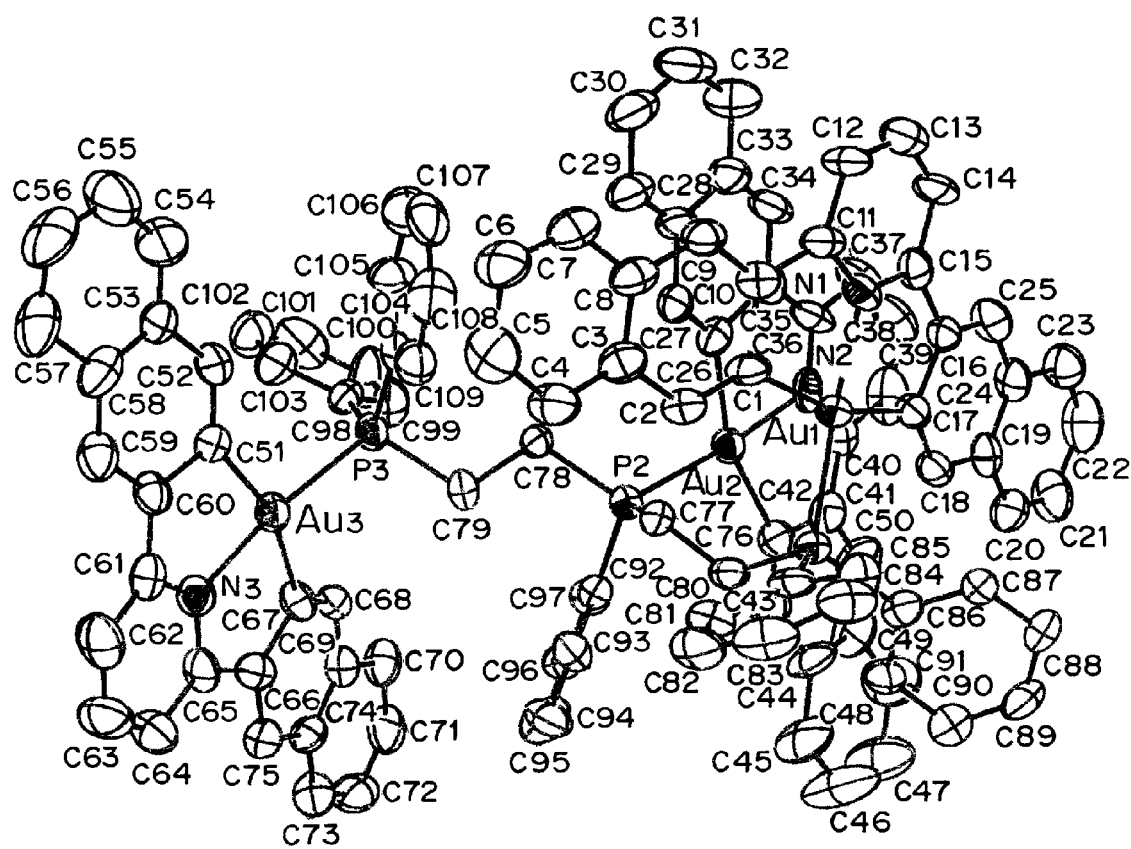
Figure 2A:
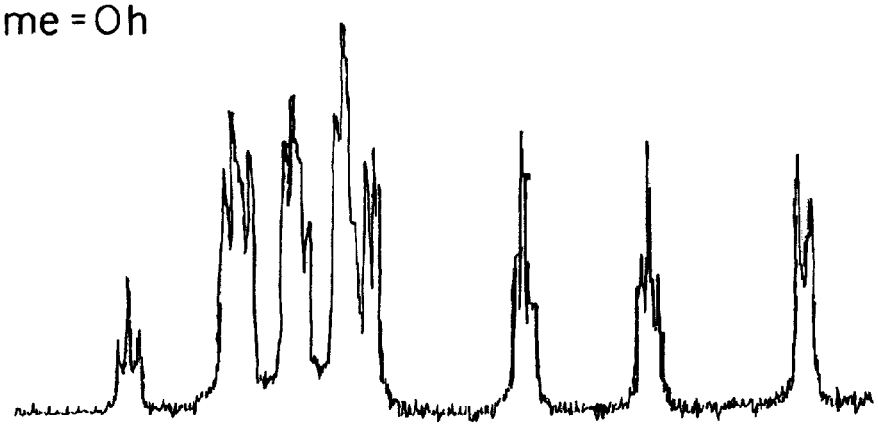
Figure 2B:
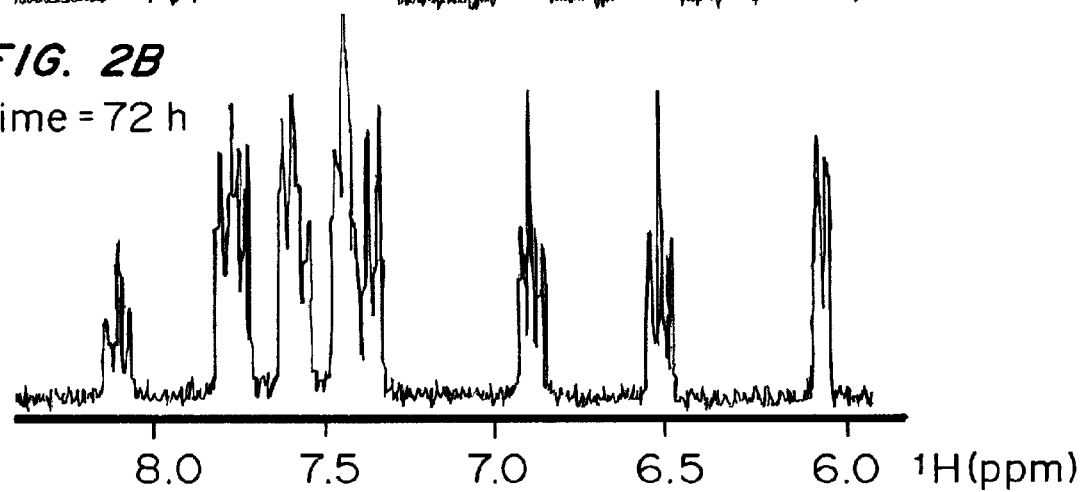

The median survival time of rats in the sham operation group was 30 days, whereas 3d at both doses of 0.5 mg/kg and 0.75 kg significantly prolonged the survival of animals (median, >40 days, FIG. 4).

What is claimed is:

1. A method for treating a tumor selected from the group consisting of hepatocellular carcinoma, nasopharyngeal carcinoma, cervical epithelioid carcinoma, and combinations thereof, in a patient in need of such treatment, comprising administering to the patient a composition comprising a pharmaceutically acceptable carrier and a therapeutically effective amount of a gold(III) complex having the structure I or structure II set out below:

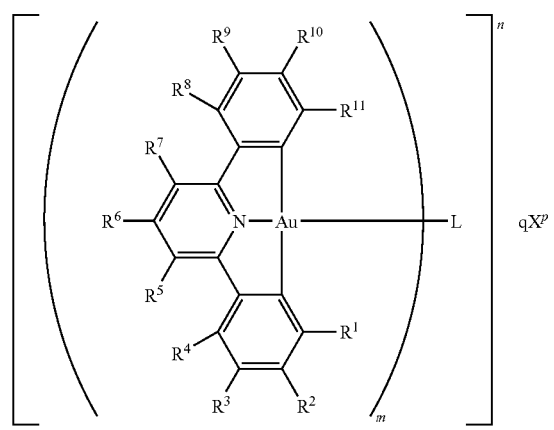

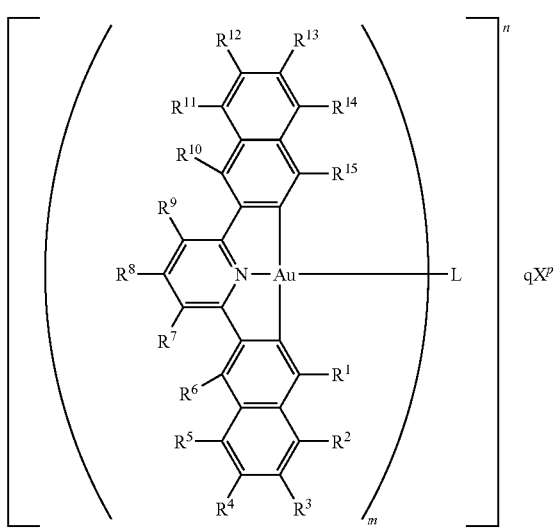

or a pharmaceutically acceptable salt thereof, wherein:

$R^1$-$R^{15}$ are each —H; m is 1; n is 0; $qX^p$ is absent; and L is

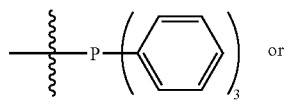

or

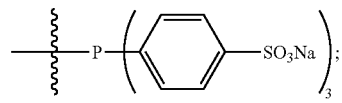

$R^1$-$R^{15}$ are each —H; m is 2; n is 2+; q is 2; $X^p$ is $CF_3SO_3^-$; and L is selected from the group consisting of

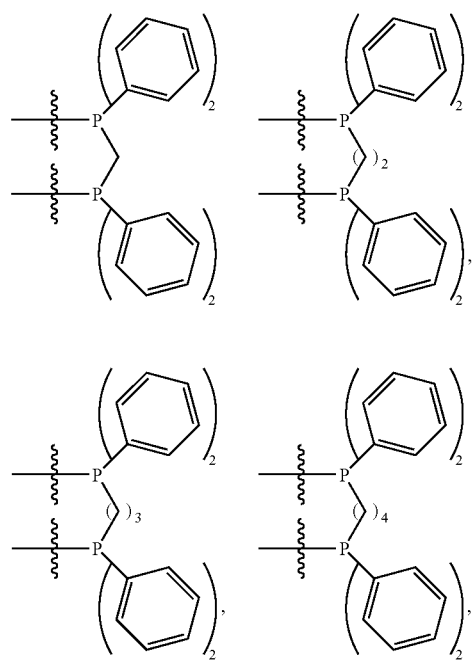

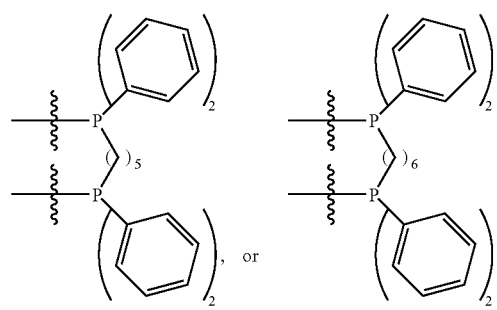

, or and each P atom is separately connected to one $[Au(CNC)]^+$ unit;

$R^1$-$R^{15}$ are each —H; m is 3; n is 3+; q is 3; $X^p$ is $CF_3SO_3^-$; and L is

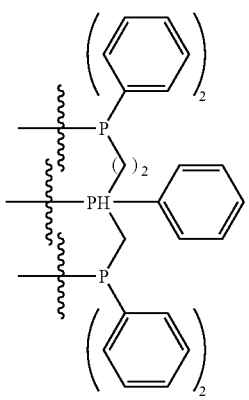

and each P atom is separately connected to one [Au(CNC)]⁺ unit;
and combinations thereof.

2. The method according to claim 1, wherein the gold(III) complexes induce apoptosis in tumor cells.

3. A pharmaceutical composition comprising a pharmaceutically acceptable carrier and an effective amount of gold compound having the following structure I or structure II:

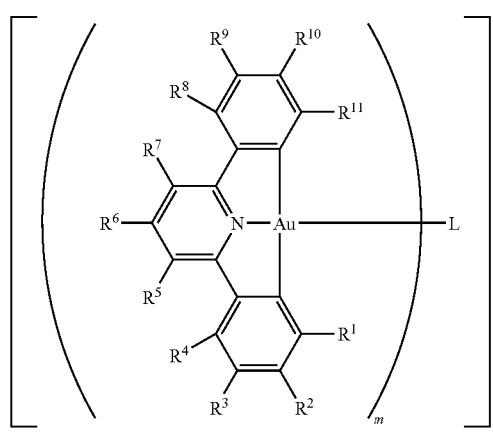

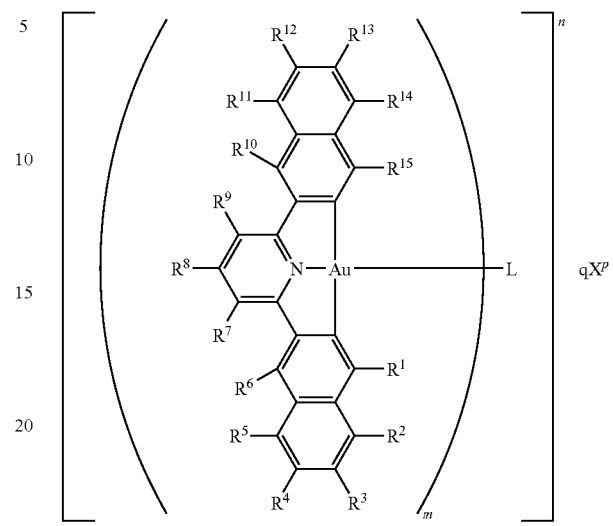

or a pharmaceutically acceptable salt thereof, wherein:
$R^1$-$R^{15}$ are each —H; m is 1; n is 0; $qX^p$ is absent; and L is

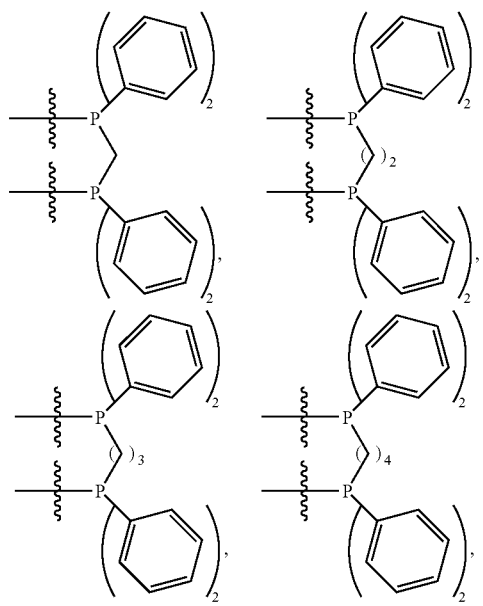

$R^1$-$R^{15}$ are each —H; m is 2; n is 2+; q is2; $X^p$ is $CF_3SO_3^-$; and L is selected from the group consisting of -continued

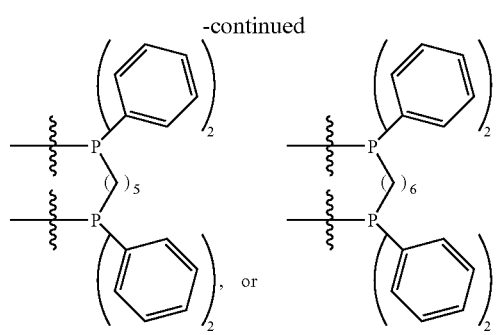

and each P atom is separately connected to one [Au(CNC)]⁺ unit;

$R^1$-$R^{15}$ are each —H; m is 3; n is 3+; q is 3; $X^p$ is $CF_3SO_3^-$; and L is

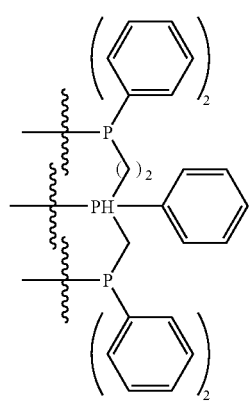

and each P atom is separately connected to one [Au(CNC)]⁺ unit;
and combinations thereof.

4. 2,6-diphenylpyridine-gold co-ordination complexes of formula I:

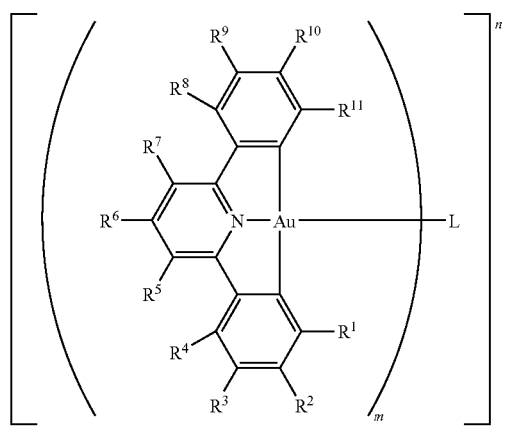

wherein each of $R^1$-$R^{11}$ is H, m is 2, n is 2+, q is 2, $X^p$ is $(CF_3SO_3)^-$ and L is a 1,2-bis(diphenylphosphino) $C^3$-$C^6$ alkane group.

5. A 2,6-diphenylpyridine-gold co-ordination complex according to claim 4 in which the group L is 1,2-bis(diphenylphosphino)propane.

6. The method of claim 1, wherein the gold(III) complex is a compound of Formula I or Formula II, wherein $R^1$-$R^{15}$ are each —H; m is 1; n is 0; $qX^p$ is absent; and L is

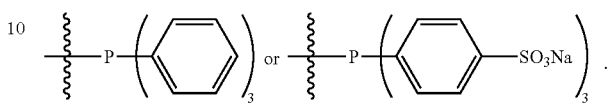

7. The method of claim 1, wherein the gold(III) complex is a compound of Formula I or Formula II, wherein $R^1$-$R^{15}$ are each —H; m is 2; n is 2+; q is 2; $X^p$ is $CF_3SO_3^-$; and L is selected from the group consisting of

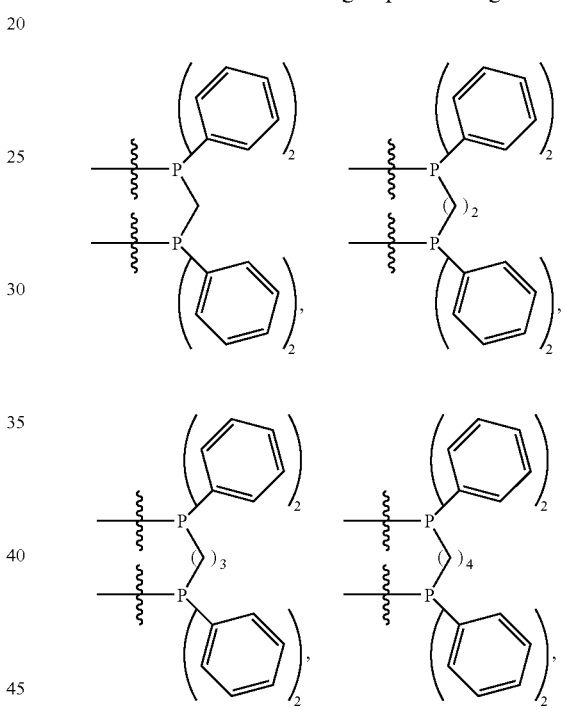

and each P atom is separately connected to one [Au(CNC)]⁺ unit.

8. The method of claim 1, wherein the gold(III) complex is a compound of Formula I or Formula II, wherein $R^1$-$R^{15}$ are each —H; m is 3; n is 3+; q is 3; $X^p$ is $CF_3SO_3^-$; and L is

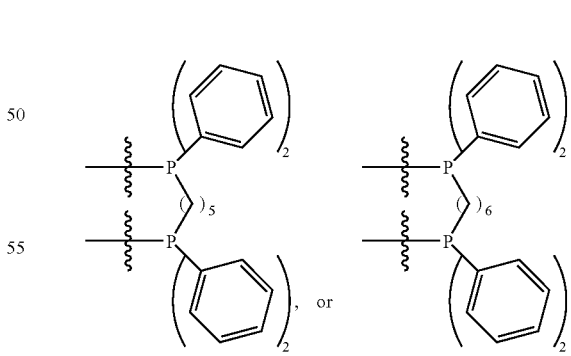

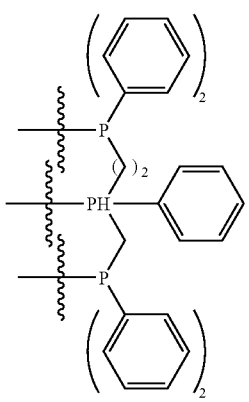

and each P atom is separately connected to one [Au(CNC)]⁺ unit.

9. The composition of claim 3, wherein the gold(III) complex is a compound of Formula I or Formula II, wherein $R^1$-$R^{15}$ are each —H; m is 1; n is 0; $qX^p$ is absent; and L is

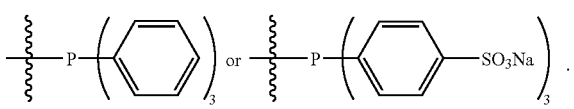

10. The composition of claim 3, wherein the gold(III) complex is a compound of Formula I or Formula II, wherein $R^1$-$R^{15}$ are each —H; m is 2; n is 2+; q is 2; $X^p$ is $CF_3SO_3^-$; and L is selected from the group consisting of

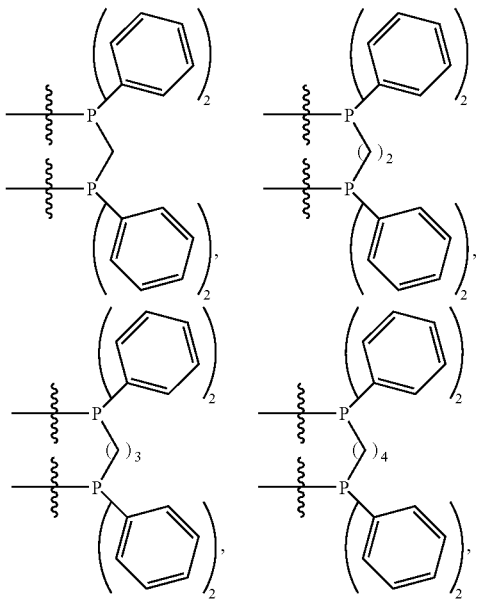

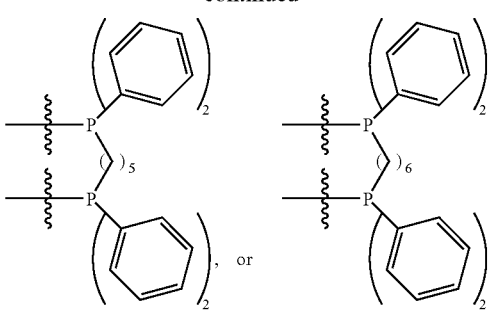

and each P atom is separately connected to one [Au(CNC)]⁺ unit.

11. The composition of claim 3, wherein the gold(III) complex is a compound of Formula I or Formula II, wherein $R^1$-$R^{15}$ are each —H; m is 3; n is 3+; q is 3; $X^p$ is $CF_3SO_3^-$; and L is

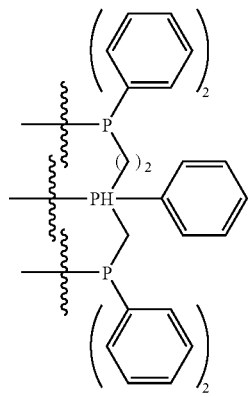

and each P atom is separately connected to one [Au(CNC)]⁺ unit.

* * * * *

UNITED STATES PATENT AND TRADEMARK OFFICE
CERTIFICATE OF CORRECTION

PATENT NO.        : 7,632,827 B2
APPLICATION NO. : 11/961631
DATED             : December 15, 2009
INVENTOR(S)       : Chi Ming Che et al.

It is certified that error appears in the above-identified patent and that said Letters Patent is hereby corrected as shown below:

Claim 1, column 23, lines 6-19,
Claim 3, column 25, lines 22-37,
Claim 8, column 27, lines 1-17, and
Claim 11, column 28, lines 33-48, replace " 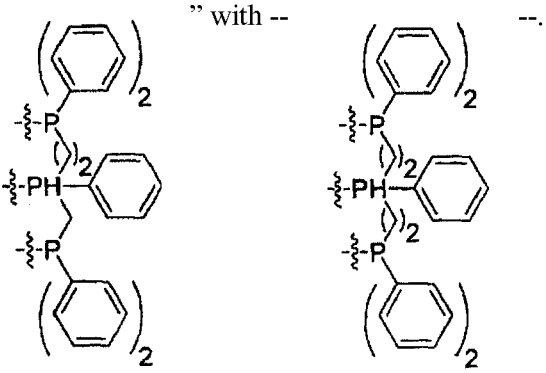 " with -- --.

Claim 3, column 24, line 40, replace "q is2" with --q is 2--.

Signed and Sealed this

Second Day of November, 2010

David J. Kappos
*Director of the United States Patent and Trademark Office*